United States Patent
Surivet et al.

(10) Patent No.: US 7,223,776 B2
(45) Date of Patent: May 29, 2007

(54) COMPOUNDS WITH ANTI-BACTERIAL ACTIVITY

(75) Inventors: Jean Phillippe Surivet, Saint-Louis (FR); Cornelia Zumbrunn, Basel (CH); Christian Hubschwerlen, Durmenach (FR); Annabelle Perez Frutos Honer, Basel (CH)

(73) Assignee: Morphochem AG, Munich (DE)

( * ) Notice: Subject to any disclaimer, the term of this patent is extended or adjusted under 35 U.S.C. 154(b) by 5 days.

(21) Appl. No.: 10/529,986

(22) PCT Filed: Oct. 9, 2003

(86) PCT No.: PCT/EP03/11203

§ 371 (c)(1),
(2), (4) Date: Mar. 31, 2005

(87) PCT Pub. No.: WO2004/035569

PCT Pub. Date: Apr. 29, 2004

(65) Prior Publication Data

US 2006/0040949 A1    Feb. 23, 2006

(30) Foreign Application Priority Data

Oct. 10, 2002 (DE) ............... 102 47 233
Dec. 2, 2002 (DE) ............... 102 56 405

(51) Int. Cl.
C07D 215/12 (2006.01)
A61K 31/47 (2006.01)

(52) U.S. Cl. ............. 514/313; 546/176; 546/177

(58) Field of Classification Search ........... 546/176, 546/177; 514/313
See application file for complete search history.

(56) References Cited

U.S. PATENT DOCUMENTS 3,184,462 A    5/1965    Scarborough et al. ... 260/256.4

FOREIGN PATENT DOCUMENTS

| FR | 2798656 | * | 3/2001 |
|---|---|---|---|
| WO | WO 96/39145 | | 12/1996 |
| WO | WO 99/37635 | | 7/1999 |
| WO | WO 00/78748 A1 | | 12/2000 |
| WO | WO200078748 | * | 12/2000 |
| WO | WO 01/07432 A2 | | 2/2001 |
| WO | WO 01/46150 A2 | | 6/2001 |
| WO | 02/08224 | * | 1/2002 |
| WO | WO 02/08224 A1 | | 1/2002 |
| WO | 02/50040 | * | 6/2002 |

OTHER PUBLICATIONS

International Search Report dated Feb. 9, 2004.

* cited by examiner

*Primary Examiner*—D. Margaret Seaman
(74) *Attorney, Agent, or Firm*—Sonnenschein Nath & Rosenthal LLP

(57) ABSTRACT

The present invention describes novel anti-bacterial compounds of formula (I).

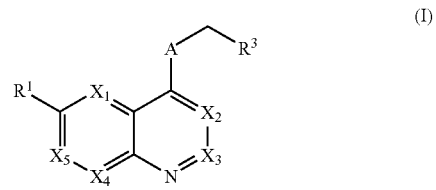

13 Claims, No Drawings

COMPOUNDS WITH ANTI-BACTERIAL ACTIVITY

Resistance to the antibiotics used currently has increased appreciably in many countries of the world in recent years and in some cases has assumed alarming proportions. The main problem is that those pathogens exhibit not just a single resistance but, as a rule, multiple resistance. This is true especially of some gram-positive pathogen groups, such as staphylococci, pneumococci and enterococci (S. Ewig et al.; Antibiotika-Resistenz bei Erregern ambulant erworbener Atemwegsinfektionen (Antibiotic resistance in pathogens of outpatient-acquired respiratory tract infections); Chemother. J. 2002, 11, 12–26; F. Tenover; Development and spread of bacterial resistance to antimicrobial agents: an overview; Clin. Infect. Dis. 2001 Sep. 15, 33 Suppl. 3, 108–115)

A long-feared development has recently occurred: In the USA, the first strain of Staphylococcus aureus has been described that is not only resistant to methicillin but also highly resistant to vancomycin (Centers for Disease Control and Prevention; Staphylococcus aureus resistant to vancomycin—United States, 2002; MMWR 2002, 51, 565–567). In addition to hygiene measures in hospitals, therefore, increased efforts are also required to find new antibiotics that as far as possible have a novel structure and a novel mechanism of action so as to be effective against those problem bacteria.

The present invention describes new kinds of compounds having anti-bacterial activity.

The present invention relates to compounds of the general formula (I):

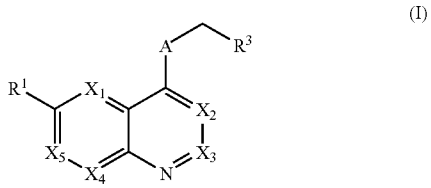

wherein

A is an oxygen, sulphur or nitrogen atom or a $C_{1-4}$alkylene, $C_{2-4}$alkenylene, $C_{2-4}$alkynylene or $C_{1-4}$heteroalkylene group, $X_1$, $X_2$, $X_3$, $X_4$ and $X_5$ are each independently of the others nitrogen atoms or groups of formula $CR_2$, $R^1$ is a hydrogen atom, a halogen atom, a hydroxy group, an alkyloxy group or a heteroalkyloxy group, $R^2$ is a hydrogen atom, a halogen atom, or a hydroxy, alkyl, alkenyl, alkynyl or heteroalkyl group, $R^3$ is selected from the following groups:

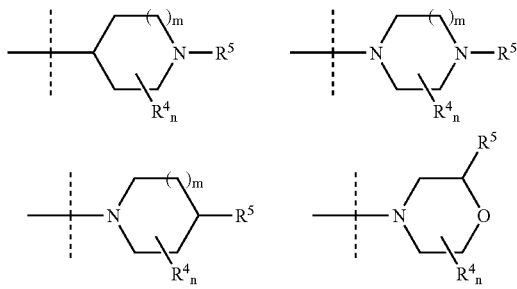

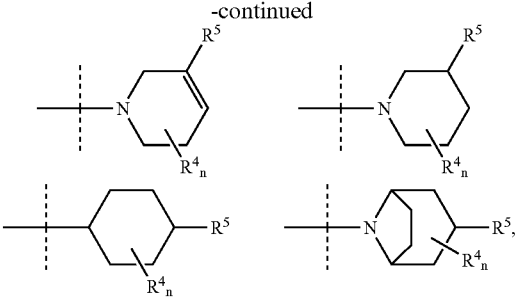

the radicals $R^4$, each independently of any other(s), are a hydroxy group, a $C_{1-6}$alkyl group or a $C_{1-8}$heteroalkyl group, $R^5$ is an alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl radical, n is 0, 1, 2 or 3 and m is 0 or 2, or a pharmacologically acceptable salt, solvate, hydrate or a pharmacologically acceptable formulation thereof.

The expression alkyl refers to a saturated, straight-chain or branched hydrocarbon group that contains from 1 to 20 carbon atoms, preferably from 1 to 12 carbon atoms, especially from 1 to 8 or from 1 to 6 or from 1 to 4 carbon atoms, for example a methyl, ethyl, propyl, isopropyl, isobutyl, tert-butyl, n-hexyl, 2,2-dimethyl-butyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 carbon atoms, for example an ethenyl, allyl, acetylenyl, propargyl, isoprenyl or hex-2-enyl group. Preferably, alkenyl groups have one or two (especially one) double bond(s) and alkynyl groups have one or two (especially one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulphur atom (preferably oxygen, sulphur or nitrogen). The expression heteroalkyl furthermore refers to a carboxylic acid or to a group derived from a carboxylic acid such as, for example, acyl, acylalkyl, alkoxycarbonyl, acyloxy, acyloxyalkyl, carboxyalkylamide or alkoxycarbonyloxy.

Examples of heteroalkyl groups are groups of formulae $R^a$—O—$Y^a$—, $R^a$—S—$Y^a$, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$, $R^a$—N($R^b$)—CO—S—$Y^a$—, $R^a$—S—CO—S—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, $R^a$ being a hydrogen atom, a $C_1$–$C_6$alkyl, a $C_2$–$C_6$alkenyl or a $C_2$–$C_6$-alkynyl group; $R^b$ being a hydrogen atom, a $C_1$–$C_6$alkyl, a $C_2$–$C_6$alkenyl or a $C_2$–$C_6$alkynyl group; $R^c$ being a hydrogen atom, a $C_1$–$C_6$alkyl, a $C_2$–$C_6$alkenyl or a $C_2$–$C_6$alkynyl group; $R^d$ being a hydrogen atom, a $C_1$–$C_6$alkyl, a $C_2$–$C_6$alkenyl or a $C_2$–$C_6$alkynyl group and $Y^a$ being a direct bond, a $C_1$–$C_6$-alkylene, a $C_2$–$C_6$alkenylene or a $C_2$–$C_6$alkynylene group, each heteroalkyl group containing at least one carbon atom and it being possible for one or more hydrogen atoms to have been replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (e.g. cycloalkenyl) cyclic group that contains one or more rings (preferably 1 or 2) containing from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH or $NO_2$ groups, thus, for example, cyclic ketones such as, for example, cyclohexanone, 2-cyclo-hexenone or cyclopentanone. Further specific examples of cycloalkyl groups are a cyclopropyl, cyclobutyl, cyclo-pentyl, spiro[4,5]decanyl, norbornyl, cyclohexyl, cyclo-pentenyl, cyclohexadienyl, decalinyl, cubanyl, bicyclo-[4.3.0]nonyl, tetralin, cyclopentylcyclohexyl, fluoro-cyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulphur atom (preferably oxygen, sulphur or nitrogen). A heterocycloalkyl group has preferably 1 or 2 ring(s) containing from 3 to 10 (especially 3, 4, 5, 6 or 7) ring atoms. The expression heterocycloalkyl refers furthermore to groups in which one or more hydrogen atoms have been replaced by fluorine, chlorine, bromine or iodine atoms or by OH, =O, SH, =S, $NH_2$, =NH or $NO_2$ groups. Examples are a piperidyl, morpholinyl, urotropinyl, pyrrolidinyl, tetrahydrothiophenyl, tetrahydropyranyl, tetrahydrofuryl, oxacyclopropyl, azacyclopropyl or 2-pyrazolinyl group and also lactams, lactones, cyclic imides and cyclic anhydrides.

The expression alkylcycloalkyl refers to groups containing both cycloalkyl and also alkyl, alkenyl or alkynyl groups in accordance with the above definitions, for example alkylcycloalkyl, alkylcycloalkenyl, alkenylcycloalkyl and alkynylcycloalkyl groups. An alkylcycloalkyl group preferably contains a cycloalkyl group that contains one or two rings systems having from 3 to 10 (especially 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulphur atom (preferably oxygen, sulphur or nitrogen). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocylcloalkenyl, the cyclic groups being saturated or mono-, di- or tri-unsaturated.

The expression aryl or Ar refers to an aromatic group that has one or more rings containing from 6 to 14 ring carbon atoms, preferably from 6 to 10 (especially 6) carbon atoms. The expression aryl (or Ar) refers furthermore to groups in which one or more hydrogen atoms have been replaced by fluorine, chlorine, bromine or iodine atoms or by OH, SH, $NH_2$ or $NO_2$ groups. Examples are a phenyl, naphthyl, biphenyl, 2-fluorophenyl, anilinyl, 3-nitrophenyl or 4-hydroxyphenyl group.

The expression heteroaryl refers to an aromatic group that has one or more rings and is formed by a ring system that contains from 5 to 14 ring atoms, preferably from 5 to 10 (especially 5 or 6) ring atoms, and contains one or more (preferably 1, 2, 3 or 4) oxygen, nitrogen, phosphorus or sulphur ring atoms (preferably O, S or N). The expression heteroaryl refers furthermore to groups in which one or more hydrogen atoms have been replaced by fluorine, chlorine, bromine or iodine atoms or by OH, SH, $NH_2$ or $NO_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetralin, dihydronaphthalene, indanone, phenylcyclopentyl, cumene, cyclohexylphenyl, fluorene and indan. An aralkyl group preferably contains one or two aromatic ring systems (1 or 2 rings) containing from 6 to 10 carbon atoms and one or two alkyl, alkenyl and/or alkynyl groups containing 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulphur atom (preferably oxygen, sulphur or nitrogen), that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing 5 or 6 to 10 carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 or those carbon atoms having been replaced by oxygen, sulphur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or triunsaturated. Specific examples are a tetrahydroisoquinolyl-, benzoyl-, 2- or 3-ethylindolyl-, 4-methylpyridino-, 2-, 3- or 4-methoxyphenyl-, 4-ethoxyphenyl-, 2-, 3- or 4-carboxyphenyl-alkyl group.

The expressions cycloalkyl, heterocycloalkyl, alkylcycloalkyl, heteroalkylcycloalkyl, aryl, heteroaryl, aralkyl and heteroaralkyl refer to groups in which one or more hydrogen atoms of such groups have been replaced by fluorine, chlorine, bromine or iodine atoms or by OH, $=O$, SH, $=S$, $NH_2$, $=NH$ or $NO_2$ groups.

The expression "optionally substituted" refers to groups in which one or more hydrogen atoms have been replaced by fluorine, chlorine, bromine or iodine atoms or by OH, $=O$, SH, $=S$, $NH_2$, $=NH$ or $NO_2$ groups. The expression refers furthermore to groups that are substituted by unsubstituted $C_1$–$C_6$alkyl, $C_2$–$C_6$alkenyl, $C_2$–$C_6$alkynyl, $C_1$–$C_6$heteroalkyl, $C_3$–$C_{10}$cycloalkyl, $C_2$–$C_9$heterocycloalkyl, $C_6$–$C_{10}$aryl, $C_1$–$C_9$heteroaryl, $C_7$–$C_{12}$aralkyl or $C_2$–$C_{11}$heteroaralkyl groups.

Owing to their substitution, compounds of formula (I) may contain one or more centres of chirality. The present invention therefore includes both all pure enantiomers and all pure diastereoisomers and also mixtures thereof in any mixing ratio. The present invention moreover also includes all cis/trans-isomers of the compounds of the general formula (I) and also mixtures thereof. The present invention moreover includes all tautomeric forms of the compounds of formula (I).

Preferred are compounds of formula (I) wherein A is an oxygen atom or a group of formula $CH_2$ or $CH(OH)$.

Also preferred are compounds of formula (I) wherein one of the groups $X_1$, $X_2$, $X_3$, $X_4$ and $X_5$ (especially $X_1$ or $X_2$) is a nitrogen atom and the others are CH groups, or all of the groups $X_1$, $X_2$, $X_3$, $X_4$ and $X_5$ are CH groups.

Furthermore, $R^3$ is preferably one of the following groups:

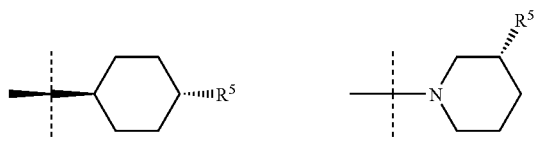

$R^1$ is especially preferably a halogen atom, a $C_{1-6}$alkyloxy group (for example methoxy or ethoxy), a methyl group or an ethyl group; especially a methoxy group.

Also preferably, $R^4$ is a $C_{1-6}$heteroalkyl group, as defined hereinabove, having one or two oxygen atoms as individual hetero atoms.

$R^4$ is especially preferably a group of formula —COOH, —CH$_2$COOH, —CH$_2$CH$_2$COOH, —CH$_2$COOCH$_3$, —CH$_2$CH$_3$, —CH$_2$OH, —CH$_2$CH$_2$OH, —OH, —OCH$_3$, —CH$_2$OCONH$_2$, —CH$_2$CH$_2$COOCH$_3$, —COOCH$_3$, —CH$_3$ or —(CH$_2$)$_3$OH.

Also preferably, n is 0 or 1.

Also preferably, $R^5$ is an aralkyl or a heteroaralkyl group.

Again preferably, $R^5$ is a group of formula —Y-Cy, Y being a $C_1$–$C_6$alkylene, $C_2$–$C_6$alkenylene or $C_1$–$C_6$heteroalkylene group, wherein optionally a hydrogen atom may have been replaced by a hydroxy group or two hydrogen atoms may have been replaced by an $=O$ group, and Cy being an optionally substituted phenyl, naphthyl or heteroaryl group containing 1 or 2 rings and from 5 to 10 ring atoms, or an optionally substituted arylheterocycloalkyl or heteroarylheterocycloalkyl group containing two rings and 9 or 10 ring atoms.

The therapeutic use of compounds of formula (I), their pharmacologically acceptable salts or solvates and hydrates and also formulations and pharmaceutical compositions also lie within the scope of the present invention.

The pharmaceutically compositions according to the present invention comprise at least one compound of formula (I) as active ingredient and, optionally, carrier substances and/or adjuvants.

Examples of pharmacologically acceptable salts of the compounds of formula (I) are salts of physiologically acceptable mineral acids, such as hydrochloric acid, sulphuric acid and phosphoric acid, and salts of organic acids, such as methanesulphonic acid, p-toluenesulphonic acid, lactic acid, acetic acid, trifluoroacetic acid, citric acid, succinic acid, fumaric acid, oxalic acid, maleic acid and salicylic acid. Further examples of pharmacologically acceptable salts of the compounds of formula (I) are alkali metal and alkaline earth metal salts such as, for example, sodium, potassium, lithium, calcium and magnesium salts, ammonium salts and salts of organic bases such as, for example, methylamine, dimethylamine, triethylamine, piperidine, ethylenediamine, lysine, choline hydroxide, meglumine, morpholine and arginine salts. Compounds of formula (I) can be solvated, especially hydrated. The hydration may take place, for example, during the preparation process or as a consequence of the hygroscopic nature of the initially anhydrous compounds of formula (I). When the compounds of formula (I) comprise asymmetric carbon atoms, they may be either in the form of achiral compounds, diastereoisomeric mixtures, mixtures of enantiomers or in the form of optically pure compounds.

The pro-drugs to which the present invention also relates consist of a compound of formula (I) and at least one pharmacologically acceptable protecting group that is removed under physiological conditions, for example an alkoxy, aralkyloxy, acyl or acyloxy group, such as, for example, an ethoxy, daloxate, benzyloxy, acetyl or acetyloxy group or a group of formula COOCH$_2$OCOC(CH$_3$)$_3$ or COOCH$_2$OCOO-cyclohexyl.

The present invention relates also to the use of those active ingredients in the preparation of medicaments. In general, compounds of formula (I) are administered either individually, or in combination with any other desired therapeutic agent, using the known and acceptable methods. Such therapeutically useful agents may be administered, for example, by one of the following routes: orally, for example in the form of dragées, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or spray, transdermally or intranasally. For the preparation of such tablets, pills, semi-solid substances, coated tablets, dragées and hard gelatin capsules, the therapeutically usable product can be mixed with pharmacologically inert, inorganic or organic pharmaceutical carrier substances, for example with lactose, sucrose, glucose, gelatin, malt, silica gel, starch or derivatives thereof, talcum, stearic acid or salts thereof, skimmed milk powder and the like. For the preparation of soft capsules, pharmaceutical carrier substances such as, for example, vegetable oils, petroleum, animal or synthetic oils, wax, fat and polyols can be used. For the preparation of liquid solutions and syrups, pharmaceutical carrier substances such as, for example, water, alcohols, aqueous saline solution, aqueous dextrose, polyols, glycerol, vegetable oils, petroleum and animal or synthetic oils can be used. For suppositories, pharmaceutical carrier substances such as, for example, vegetable oils, petroleum, animal or synthetic oils, wax, fat and polyols can be used. For aerosol formulations, compressed gases that are suitable for the purpose can be used, such as, for example, oxygen, nitrogen and carbon dioxide. The pharmaceutically acceptable agents may also comprise additives for preserving and stabilising, emulsifiers, sweeteners, flavourings, salts for altering the osmotic pressure, buffers, encapsulation additives and antioxidants.

Combinations with other therapeutic agents may comprise other antimicrobial and anti-fungal active ingredients.

For the prevention and/or treatment of bacterial infections, the dose of the biologically active compound according to the invention can vary within wide limits and can be adjusted to individual requirements. Generally, a dose of from 10 mg to 4000 mg per day is suitable, a preferred dose being from 50 to 3000 mg per day. In suitable cases, the dose may also be below or above the stated values. The daily dose can be administered as a single dose or in a plurality of doses. A typical individual dose contains approximately 50 mg, 100 mg, 250 mg, 500 mg, 1 g or 2 g of the active ingredient.

EXAMPLES

Example 1

2-((3RS)-{[(2,3-Dihydro-benzo[1,4]dioxin-6-yl-methyl)amino]methyl}piperidin-1-yl)-(1RS)-(6-methoxy-quinolin-4-yl)ethanol 1.a) Benzyl (3RS)-azidomethylpiperidine-1-carbamate

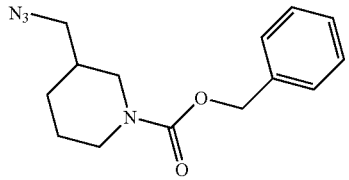

At 0° C., triethylamine (5.6 ml, 40.1 mmol) and then methanesulphonyl chloride (2 ml, 25.7 mmol) were added to a solution of benzyl 3-hydroxymethylpiperidine-1-carbamate (5 g, 20.05 mmol) in dichloromethane (100 ml). After the solution had been stirred for 20 min., the reaction mixture was cooled to −60° C. and a solution of benzyl 4-oxopiperidine-1-carbamate (2.33 g, 10 mmol) in diethyl ether (10 ml) was added. The reaction mixture was heated to room temperature in the course of 30 minutes and water (40 ml) was added. The two phases were separated and the aqueous phase was extracted twice using 50 ml of ethyl acetate each time. The combined organic phases were washed with 20 ml of saturated sodium chloride solution, dried over MgSO$_4$, filtered and concentrated to dryness by rotary evaporation. The residue was purified by column chromatography on silica gel (EtOAc). The resulting oil was dissolved in DMF (45 ml), and sodium azide (2.6 g, 40 mmol) was added. The reaction mixture was further stirred for 3 hours at 80° C. and then diluted with water (100 ml) and ethyl acetate (200 ml). The two phases were separated and the aqueous phase was extracted twice using 50 ml of ethyl acetate each time. The combined organic phases were washed with 20 ml of saturated sodium chloride solution, dried over MgSO$_4$, filtered and concentrated to dryness by rotary evaporation. The residue was purified by column chromatography on silica gel (hexane/EtOAc 1/1).

Yield: 6.1 g (18.6 mmol) $^1$H-NMR (CDCl$_3$, 300 MHz: 1.28 (m, 1H); 1.51 (m, 1H); 1.60–1.87 (m, 3H); 2.74 (br s, 1H); 2.91 (m, 1H); 3.23 (br d, J=4.5 Hz, 2H); 3.98 (td, J=4.1, 13.2 Hz, 1H); 4.06 (br s, 1H); 5.15 (s, 2H); 7.28–7.38 (m, 5H).

Benzyl 3-hydroxymethyl-piperidine-1-carbamate has already been described in *Arch. Pharm.* (Weinheim, Germany) 1990 p. 9–12.

1.b) Benzyl (3RS)-aminomethyl-piperidine-1-carbamate

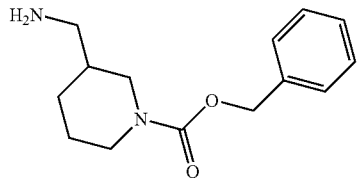

Triphenylphosphine (8 g, 30 mmol) was added to a solution of benzyl 3-azidomethylpiperidine-1-carbamate (6.1 g, 18.6 mmol) in THF (37 ml) and water (5 ml). After the solution had been stirred for 3 hours at 60° C., the reaction mixture was concentrated and the residue was taken up in 3N HCl (200 ml) and ether (200 ml). The two phases were separated and the aqueous phase was extracted twice using 100 ml of ethyl acetate each time. Solid sodium hydroxide (16 g, 640 mmol) was cautiously added until an oil separated out. The mixture was diluted with ethyl acetate and the organic phases was dried over MgSO$_4$ and filtered, and the filtrate was concentrated to dryness by rotary evaporation.

Yield: 2.81 g, 11.3 mmol MS (EI) m/z 249 [M+H]$^+$ 1.c) Benzyl (3RS)-{[(2,3-dihydrobenzo[1,4]dioxin-6-ylmethyl)-amino]-methyl}-piperidine-1-carbamate

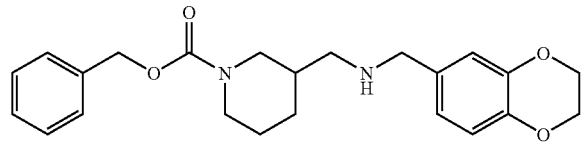

1,4-Benzodioxane-6-carbaldehyde (0.984 g, 6 mmol) and sodium triacetoxyborohydride (1.7 g, 8 mmol) were added to a solution of benzyl 3-aminomethylpiperidine-1-carbamate (1.5 g, 6 mmol) in dichloroethane (37 ml) and THF (4 ml). After the solution had been stirred at room temperature for 3 hours, saturated NaHCO$_3$ solution (20 ml) was added. The two phases were separated and the aqueous phase was extracted twice using 50 ml of dichloromethane each time. The combined organic phases were washed with 20 ml of saturated sodium chloride solution, dried over MgSO$_4$, filtered and concentrated to dryness by rotary evaporation. The residue was purified by column chromatography on silica gel (EtOAc and then MeOH/EtOAc 1/9).

Yield: 1.7 g, 4.28 mmol (oil) MS (EI) m/z 397 [M+H]$^+$

1.d (2,3-Dihydro-benzo[1,4]dioxin-6-ylmethyl)-piperidin-(3RS)-yl-methylamine

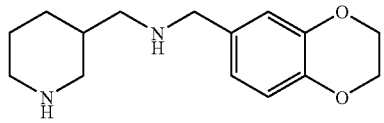

20% Pd(OH)₂ on carbon (0.23 g) was added to a solution of benzyl 3-{[(2,3-dihydrobenzo[1,4]dioxin-6-yl-methyl)-amino]methyl}piperidine-1-carbamate (0.98 g, 2.47 mmol) in EtOH (10 ml) and EtOAc (10 ml) and hydrogenation was carried out under a hydrogen atmosphere (1 bar). The reaction mixture was filtered and the filtrate was concentrated.

Yield: 0.64 g, 2.43 mmol MS (EI) m/z 308 [M+H]⁺

1.e) (RS)-6-Methoxy-4-oxiranylquinoline

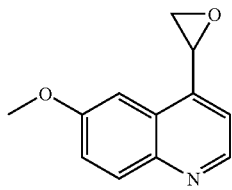

Trimethylsulphonium iodide (0.954 g, 4.67 mmol) and potassium hydroxide powder (1.8 g, 32 mmol) were added to a solution of 6-methoxy-quinoline-4-carbaldehyde (0.85 g, 4.54 mmol) in acetonitrile (13.5 ml) and water (6 drops). The reaction mixture was heated at 60° C. for one hour. The mixture was then cooled to room temperature and benzene (40 ml) was added. The precipitate was filtered off and the filtrate was concentrated to dryness by rotary evaporation. The residue was diluted with water (100 ml) and ethyl acetate (100 ml), the phases were separated, and the aqueous phase was extracted twice using 50 ml of ethyl acetate each time. The combined organic phases were dried over MgSO₄, filtered and concentrated to dryness by rotary evaporation. The residue was purified by column chromatography on silica gel (EtOAc).

Yield: 0.904 g, 4.5 mmol MS (EI) m/z 202 [M+H]⁺

6-Methoxyquinoline-4-carbaldehyde was prepared according to *Eur. J. Med. Chem. Chim. Ther.* 2000 (35) p-707–714.

1.f) 2-((3RS)-{[(2,3-Dihydrobenzo[1,4]dioxin-6-ylmethyl)-amino]-methyl}-piperidin-1-yl)-(1RS)-(6-methoxy-quinolin-4-yl)ethanol

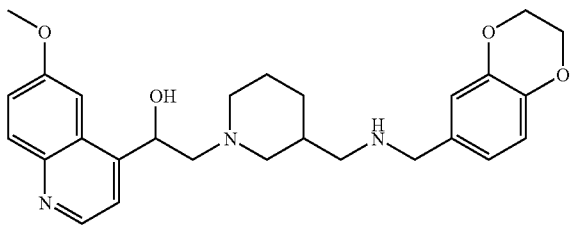

A solution of (RS)-6-methoxy-4-oxiranylquinoline (0.161 g, 0.8 mmol) and (2,3-dihydrobenzo[1,4]dioxin-6-ylmethyl)-piperidin-(3RS)-ylmethylamine (0.210 g, 0.8 mmol) in ethanol (4 ml) was heated at 80° C. for 16 hours. The reaction mixture was cooled to room temperature and concentrated to dryness by rotary evaporation. The residue was purified by column chromatography on silica gel (EtOAc and then EtOAc/MeOH 4:1).

Yield: 0.240 g. 0.51 mmol (oil) MS (EI) m/z 464 [M+H]⁺

Example 2

(1RS)-(6-Methoxy-quinolin-4-yl)-2-((3RS)-{[(naphth-2-ylmethyl)-amino]-methyl}-piperidin-1-yl)-ethanol

2.a) Benzyl (3RS)-(tert-butoxycarbonylamino-methyl)-piperidine-1-carbamate

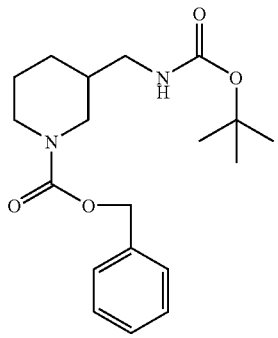

Triethylamine (5.6 ml) and di-tert-butyl dicarbonate (4.9 g, 22.4 mmol) were added to a solution of benzyl 3-aminomethylpiperidine-1-carbamate (5 g, 20.1 mmol) in dichloromethane (100 ml). After the solution had been stirred at room temperature for 4 hours, the solution was concentrated to dryness by rotary evaporation. The residue was purified by column chromatography on silica gel (EtOAc/hexane 1/4).

Yield: 5.0 g, 14.3 mmol (oil) MS (EI) m/z 349 [M+H]⁺

2.b) tert-Butyl (RS)-piperidin-3-ylmethylcarbamate

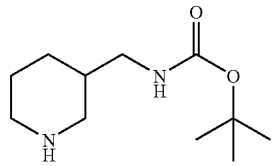

20% Pd(OH)₂ on carbon (1 g) was added to a solution of benzyl 3-(tert-butoxycarbonylamino-methyl)-piperidine-1-carbamate (5 g, 14.3 mmol) in EtOH (50 ml) and EtOAc (50 ml), and hydrogenation was carried out under a hydrogen atmosphere (1 bar). The reaction mixture was filtered and the filtrate was concentrated.

Yield: 3.0 g, 14 mmol (oil) MS (EI) m/z 215 [M+H]⁺

2.c) tert-Butyl {1-[(2RS)-hydroxy-2-(6-methoxy-quinolin-4-yl)-ethyl]-piperidin-(3RS)-ylmethyl}carbamate

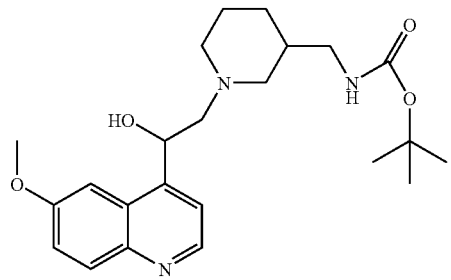

A solution of 6-methoxy-4-oxiranylquinoline (2.68 g, 13.3 mmol) and tert-butyl piperidin-3-ylmethylcarbamate (2.85 g, 13.3 mmol) in ethanol (35 ml) was heated at 80° C.

for 12 hours. The reaction mixture was cooled to room temperature and concentrated to dryness by rotary evaporation. The residue was purified by column chromatography on silica gel (dichloromethane/MeOH 9:1).

Yield: 2.49 g. 6 mmol (foam) MS (EI) m/z 416 [M+H]$^+$ 2.d) 2-((3RS)-Aminomethyl-piperidin-1-yl)-(1RS)-(6-methoxy-quinolin-4-yl)-ethanol

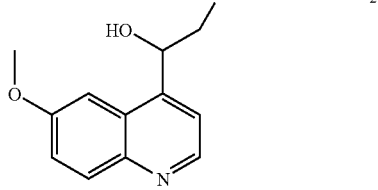

A solution of tert-butyl {1-[2-hydroxy-2-(6-methoxy-quinolin-4-yl)-ethyl]-piperidin-3-ylmethyl}carbamate (2.49 g, 6 mmol) in TFA (10 ml) was stirred at room temperature for 20 minutes. The reaction mixture was concentrated and taken up in aqueous 2N NaOH. The aqueous phase was extracted with dichloromethane/MeOH (9/1), and the combined organic phases were dried over sodium sulphate, filtered and concentrated to dryness by rotary evaporation.

Yield: 1.7 g. 5.4 mmol (foam) MS (EI) m/z 316 [M+H]$^+$ 2.e) (1RS)-(6-Methoxy-quinolin-4-yl)-2-((3RS)-{[(naphth-2-ylmethyl)-amino]-methyl}-piperidin-1-yl)-ethanol

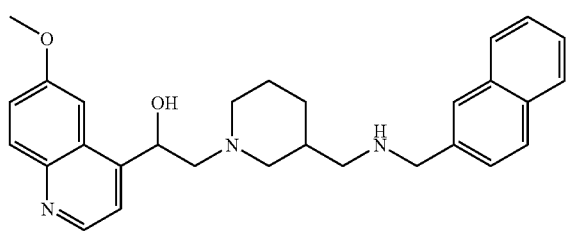

Molecular sieve, type 3A, (1 g) and 2-naphthaldehyde (0.078 g, 0.5 mmol) were added to a solution of 2-(3-aminomethyl-piperidin-1-yl)-1-(6-methoxy-quinolin-4-yl)-ethanol (0.158 g, 0.5 mmol) in MeOH (1.5 ml) and dichloromethane (3.5 ml). The reaction mixture was stirred at room temperature for 16 hours and sodium borohydride (0.05 g, 1.35 mmol) was added. The reaction mixture was stirred at room temperature for 2 hours and then filtered over Hydromatrix (wetted with a NaHCO$_3$ solution, 2 ml) and subsequently washed with dichloromethane. The filtrate was concentrated to dryness by rotary evaporation. The residue was purified by column chromatography on silica gel (dichloromethane/MeOH 9/1 1% NH$_4$OH).

Yield: 0.158 g. (0.34 mmol) (foam) MS (EI) m/z 456 [M+H]$^+$

Example 3

(1RS)-(6-Methoxy-quinolin-4-yl)-2-{(3RS)-[(3-phenyl-allylamino)-methyl]-piperidin-1-yl}-ethanol

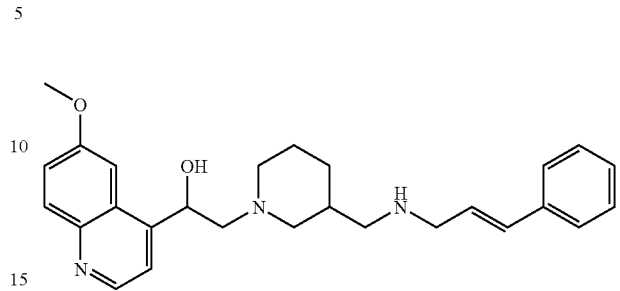

In an analogous manner, starting from Example 2.e, (1RS)-(6-methoxy-quinolin-4-yl)-(2RS)-{3-[(3-phenyl-allylamino)-methyl]-piperidin-1-yl}-ethanol was produced in a yield of 74% (MS (EI) m/z 432 [M+H]$^+$).

Example 4

2-{(3RS)-[(3-Furan-2-yl-allylamino)-methyl]-piperidin-1-yl}-(1RS)-(6-methoxy-quinolin-4-yl)-ethanol

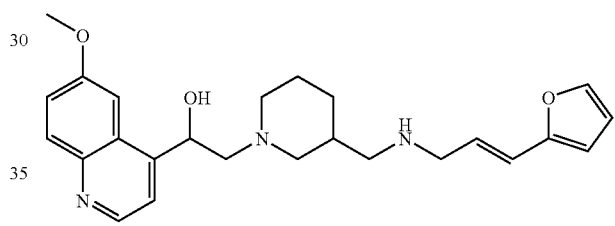

In an analogous manner, starting from Example 2.e, 2-{3-[(3-furan-2-yl-allylamino)-methyl]-piperidin-1-yl}-1-(6-methoxy-quinolin-4-yl)-ethanol was produced in a yield of 56% (MS (EI) m/z 422 [M+H]$^+$).

Example 5

(3S)-6-[({1-[2-Hydroxy-2-(6-methoxy-quinolin-4-yl)-ethyl]-piperidin-(3RS)-ylmethyl}-amino)-methyl]-4H-benzo[1,4]oxazin-3-one 5 a) tert-Butyl (3S)-aminomethyl-piperidine-1-carbamate

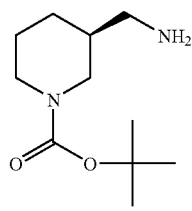

Triphenylphosphine (3.93 g, 15 mmol) was added to a solution of tert-butyl (3R)-azidomethylpiperidine-1-carbamate (2.16 g, 8.9 mmol) in THF (60 ml) and water (5 ml). After the solution had been stirred at 60° C. for 3 hours, the reaction mixture was concentrated and the residue was taken up in 3N HCl (200 ml) and ether (200 ml). The two phases were separated and the aqueous phase was extracted twice using 100 ml of ethyl acetate each time. Solid sodium hydroxide (6 g, 150 mmol) was cautiously added until an oil separated out. The mixture was diluted with ethyl acetate, the organic phase was dried over MgSO$_4$ and filtered and the filtrate was concentrated to dryness by rotary evaporation.

Yield: 1.90 g, 8.8 mmol MS (EI) m/z 215 [M+H]$^+$ tert-Butyl 3R-azidomethyl-piperidine-1-carbamate was prepared according to *J. Med. Chem.* 1994 (37) p. 3889–3901

5.b) tert-Butyl 3S-(benzyloxycarbonylamino-methyl)-piperidine-1-carbamate

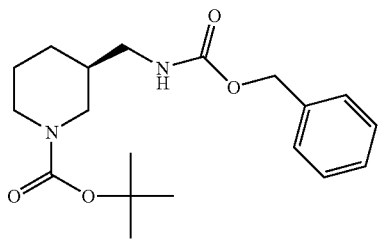

Sodium bicarbonate (1.3 g, 15.4 mmol) and chloroformic acid benzyl ester (1.3 ml, 9 mmol) were added to a solution of tert-butyl 3S-aminomethyl-piperidine-1-carbamate (1.90 g, 8.8 mmol) in acetone/water (1/1, 100 ml). The reaction mixture was stirred for one hour and then concentrated to dryness by rotary evaporation. The residue was diluted with EtOAc (100 ml). The two phases were separated and the aqueous phase was extracted twice using 50 ml of EtOAc each time. The combined organic phases were washed with 20 ml of saturated sodium chloride solution, dried over MgSO$_4$, filtered and concentrated to dryness by rotary evaporation. The residue was purified by column chromatography on silica gel (EtOAc/hexane 1/2).

Yield: 2.96 g, 8.5 mmol (oil) MS (EI) m/z 349 [M+H]$^+$

5.c) Benzyl piperidin-(3R)-ylmethylcarbamate

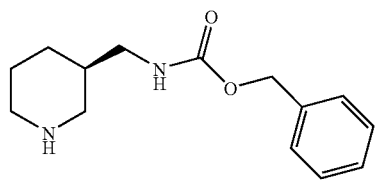

A solution of tert-butyl 3S-(benzyloxycarbonylaminomethyl)-piperidine-1-carbamate (2.96 g, 6 mmol) in TFA (10 ml) was stirred at room temperature for 20 minutes. The reaction mixture was concentrated and taken up in aqueous 2N NaOH. The aqueous phase was extracted with dichloromethane/MeOH (9/1), and the combined organic phases were dried over sodium sulphate, filtered and concentrated to dryness by rotary evaporation.

Yield: 1.96 g. 7.9 mmol (foam) MS (EI) m/z 249 [M+H]$^+$

5.d) Benzyl {1-[(2RS)-hydroxy-2-(6-methoxy-quinolin-4-yl)-ethyl]-piperidin-(3R)-ylmethyl}carbamate

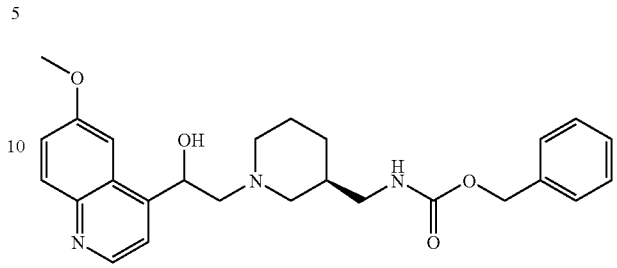

Potassium carbonate (1.12 g, 8.10 mmol) and lithium perchlorate (0.627 g, 5.89 mmol) were added to a solution of 6-methoxy-4-oxiranylquinoline (1.127 g, 5.60 mmol) and benzyl piperidin-3-ylmethylcarbamate (1.46 g, 5.88 mmol) in DMF (17 ml). The reaction mixture was heated at 60° C. for 16 hours and then cooled to room temperature and concentrated to dryness by rotary evaporation. The residue was purified by column chromatography on silica gel (dichloromethane/MeOH 9:1 1% ammonium hydroxide).

Yield: 2.51 g. 5.58 mmol (oil) MS (EI) m/z 450 [M+H]$^+$

5.e) (3S)-2-(3-Aminomethyl-piperidin-1-yl)-(1RS)-(6-methoxy-quinolin-4-yl)-ethanol

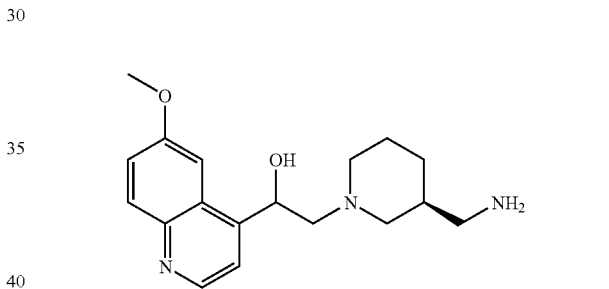

20% Pd(OH)$_2$ on carbon (0.7 g) was added to a solution of benzyl {1-[2-hydroxy-2-(6-methoxy-quinolin-4-yl)-ethyl]-piperidin-3-ylmethyl}carbamate (2.51 g, 5.58 mmol) in THF (35 ml), MeOH (7 ml) was added and hydrogenation was carried out under a hydrogen atmosphere (1 bar). The reaction mixture was filtered and the filtrate was concentrated.

Yield: 1.76 g. 5.58 mmol (oil) MS (EI) m/z 316 [M+H]$^+$

5.f) (3S)-6-[({1-[(2RS)-Hydroxy-2-(6-methoxy-quinolin-4-yl)-ethyl]-piperidin-3-ylmethyl}-amino)-methyl]-4H-benzo[1,4]oxazin-3-one

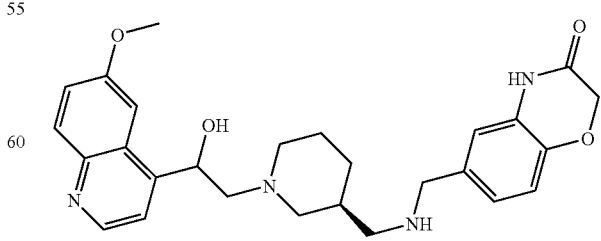

Molecular sieve, type 3A, (1.082 g) and 3-oxo-3,4-dihydro-2H-benzo[1,4]oxazine-6-carbaldehyde (0.095 g, 0.54 mmol) were added to a solution of (3S)-2-(3-aminomethylpiperidin-1-yl)-1-(6-methoxy-quinolin-4-yl)-ethanol (0.171 g, 0.54 mmol) in MeOH (1.6 ml) and dichloromethane (3.8 ml). The reaction mixture was stirred at room temperature for 16 hours and sodium borohydride (0.054 g, 1.43 mmol) was added. The reaction mixture was stirred at room temperature for 2 hours and then filtered over Hydromatrix (wetted with an NaHCO$_3$ solution, 2 ml) and subsequently washed with dichloromethane. The filtrate was concentrated to dryness by rotary evaporation. The residue was purified by column chromatography on silica gel (dichloromethane/ MeOH 9/1 1% NH$_4$OH).

Yield: 0.112 g. (0.24 mmol) (foam) MS (EI) m/z 477 [M+H]$^+$

3-Oxo-3,4-dihydro-2H-benzo[1,4]oxazine-6-carbaldehyde was prepared according to WO 02/34754.

Example 6

(3S)-2-(3-{[(Benzo[1,2,5]thiadiazol-5-ylmethyl)-amino]-methyl}-piperidin-1-yl)-(1RS)-(6-methoxy-quinolin-4-yl)-ethanol

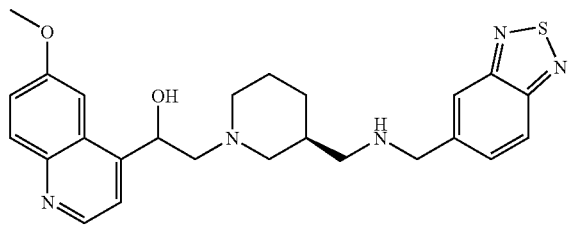

Starting from (3S)-2-(3-aminomethyl-piperidin-1-yl)-1-(6-methoxy-quinolin-4-yl)-ethanol (Example 5.e), (3S)-2-(3-{[(benzo[1,2,5]thiadiazol-5-ylmethyl)-amino]-methyl}-piperidin-1-yl)-1-(6-methoxy-quinolin-4-yl)-ethanol was produced in an analogous manner in a yield of 49% (MS (EI) m/z 464 [M+H]$^+$).

Example 7

2-((3S)-{[(2,3-Dihydro-benzo[1,4]dioxepin-6-ylmethyl)-amino]-methyl}-piperidin-1-yl)-(1RS)-(6-methoxy-quinolin-4-yl)-ethanol

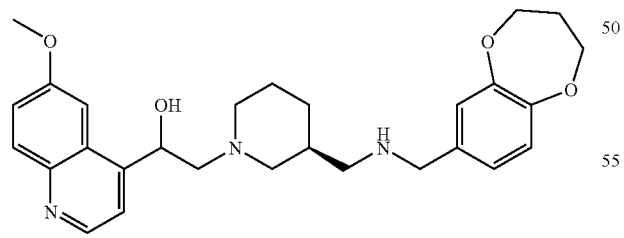

Starting from (3S)-2-(3-aminomethyl-piperidin-1-yl)-1-(6-methoxy-quinolin-4-yl)-ethanol (Example 5.e), 2-((3S)-{[(2,3-dihydro-benzo[1,4]dioxepin-6-ylmethyl)-amino]-methyl}-piperidin-1-yl)-(1RS)-(6-methoxy-quinolin-4-yl)-ethanol was produced in an analogous manner in a yield of 62% (MS (EI) m/z 478 [M+H]$^+$).

3,4-Dihydro-2H-benzo[b][1,4]dioxepine-7-carbaldehyde was prepared according to *Chem. Abstr* 1958, 3816.

Example 8

2-((3S)-{[(2,3-Dihydro-benzo[1,4]dioxin-6-ylmethyl)-amino]-methyl}-piperidin-1-yl)-(1S)-(6-methoxy-quinolin-4-yl)-ethanol 8.a) tert-Butyl (3S)-{[(2,3-dihydro-benzo[1,4]dioxin-6-ylmethyl)-amino]-methyl}-piperidine-1-carbamate

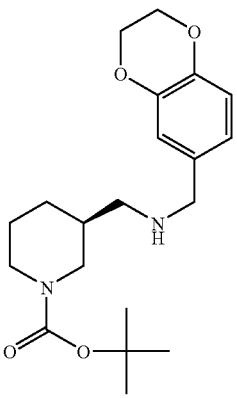

Molecular sieve, type 3A, (9.6 g) and 2,3-dihydro-benzo[1,4]dioxin-6-carbaldehyde (0.078 g, 0.5 mmol) were added to a solution of tert-butyl 3S-aminomethyl-piperidine-1-carbamate (Example 5.a) (0.158 g, 0.5 mmol) in MeOH (8 ml) and dichloromethane (27 ml). The reaction mixture was stirred at room temperature for 16 hours and sodium borohydride (0.05 g, 1.35 mmol) was added. The reaction mixture was stirred at room temperature for 2 hours and then filtered over Hydromatrix (wetted with an NaHCO$_3$ solution, 20 ml) and subsequently washed with dichloromethane. The filtrate was concentrated to dryness by rotary evaporation. The residue was purified by column chromatography on silica gel (dichloromethane/MeOH 19/1).

Yield: 2.2 g. 6.0 mmol (foam) MS (EI) m/z 363.4 [M+H]$^+$ 8.b) (R)-(2,3-Dihydro-benzo[1,4]dioxin-6-ylmethyl)-piperidin-3-ylmethyl-amine

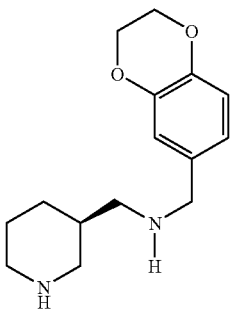

A solution of tert-butyl 3S-{[(2,3-dihydro-benzo[1,4]-dioxin-6-ylmethyl)-amino]-methyl}-piperidine-1-carbamate (2.2 g, 6 mmol) in TFA (10 ml) was stirred at room temperature for 20 minutes. The reaction mixture was concentrated and taken up in aqueous 2N NaOH. The aqueous phase was extracted with dichloromethane/MeOH (9/1), and the combined organic phases were dried over sodium sulphate, filtered and concentrated to dryness by rotary evaporation.

Yield: 1.18 g, 4.53 mmol (foam) MS (EI) m/z 263.4 [M+H]$^+$

8.c) 2-((3S)-{[(2,3-Dihydro-benzo[1,4]dioxin-6-ylmethyl)amino]-methyl}-piperidin-1-yl)-(1S)-(6-methoxy-quinolin-4-yl)-ethanol

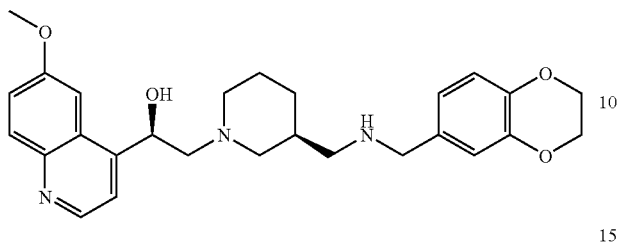

The title compound was produced in a manner analogous to Example 1.f in a yield of 36% (MS (EI) m/z 464.5 [M+H]$^+$).

(R)-6-Methoxy-4-oxiranylquinoline was prepared analogously to WO 02/50040.

Example 9

2-((3S)-{[(2,3-Dihydro-benzo[1,3]dioxo-6-ylmethyl)-amino]-methyl}-piperidin-1-yl)-(1RS)-(6-methoxy-quinolin-4-yl)-ethanol

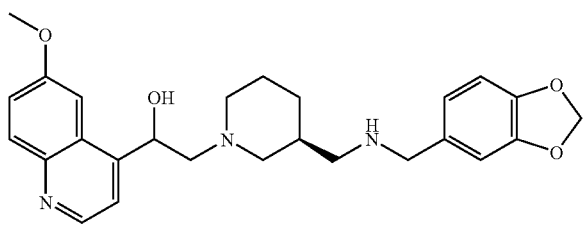

The title compound was produced in a manner analogous to Example 1f in a yield of 44% (MS (EI) m/z 450 [M+H]$^+$).

Example 10

4-[(Benzo[1.3]dioxol-5-ylmethyl)-amino]-1-[2-(6-methoxy-quinazolin-4-yl)-ethyl]-cyclohexanol

10.a) 8-([2-(6-Methoxy-quinazolin-4-yl)-ethyl]-1,4-dioxaspiro-[4.5]decan-8-ol

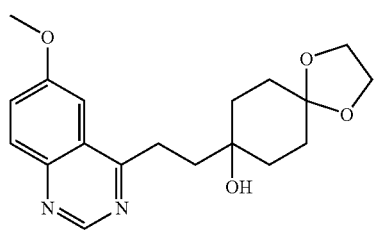

Platinum oxide (0.46 g) was added to a solution of 8-(6-methoxy-quinazolin-4-ylethynyl)-1,4-dioxa-spiro[4.5]decan-8-ol (0.96 g, 2.88 mmol) in EtOH (40 ml) and THF (10 ml), and hydrogenation was carried out under a hydrogen atmosphere (1 bar). The reaction mixture was stirred in the presence of activated carbon (5 g) and filtered. The filtrate was concentrated to dryness by rotary evaporation. The residue was purified by column chromatography on silica gel (EtOAc and then EtOAc:MeOH 9/1).

Yield: 0.623 g (1.81 mmol), foam MS (EI) m/z 344 [M+H]$^+$ 8-(6-Methoxy-quinazolin-4-ylethynyl)-1,4-dioxa-spiro-[4.5]decan-8-ol was prepared according to J. Chem. Soc. Perk. Trans. 1, 2000, 3382.

10.b) 4-Hydroxy-4-[2-(6-methoxyquinazolin-4-yl)-ethyl]-cyclo-hexanone

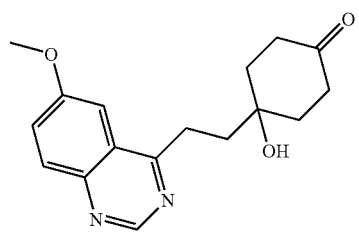

A solution of 8-([2-(6-methoxy-quinazolin-4-yl)-ethyl]-1,4-dioxa-spiro[4.5]decan-8-ol (0.623 g, 1.81 mmol) in AcOH/THF/H$_2$O (3/2/2, 10 ml) was stirred at 60° C. for 30 hours. The reaction mixture was concentrated to dryness by rotary evaporation. The residue was diluted with sodium bicarbonate (100 ml) and ethyl acetate (100 ml), the phases were separated and the aqueous phase was extracted twice using 50 ml of ethyl acetate each time. The combined organic phases were dried over MgSO$_4$, filtered and concentrated to dryness by rotary evaporation.

Yield: 0.425 g (1.41 mmol) foam. MS (EI) m/z 301 [M+H]$^+$

10.c) 4-[(Benzo[1.3]dioxol-5-ylmethyl)-amino]-1-[2-(6-methoxy-quinazolin-4-yl)-ethyl]-cyclohexanol

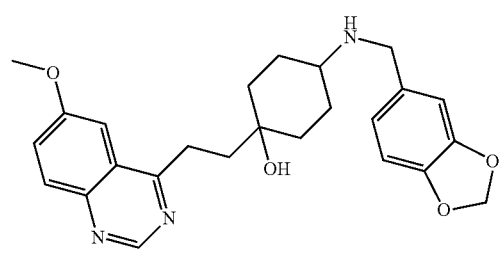

Piperonylamine (0.030 ml, 0.24 mmol) and sodium triacetoxyborohydride (0.08 g, 0.377 mmol) were added to a solution of 4-hydroxy-4-[2-(6-methoxy-quinazolin-4-yl)-ethyl]-cyclohexanone (0.06 g, 0.2 mmol) in dichloromethane (1 ml). The reaction mixture was stirred overnight and then filtered over Hydromatrix (wetted with an NaHCO$_3$ solution, 2 ml) and subsequently washed with dichloromethane. The filtrate was concentrated to dryness by rotary evaporation. The residue was purified by column chromatography on silica gel (dichloromethane:MeOH 9/1 and then dichloromethane:MeOH 9/1 and 2% triethylamine).

Yield: 0.074 g (0.17 mmol) cis/trans mixture MS (EI) m/z 436 [M+H]$^+$

Example 11

4-[(Benzo[1,2,5]thiadiazol-5-ylmethyl)-amino]-1-[2-(6-methoxy-quinazolin-4-yl)-ethyl]-cyclohexanol

11.a) 4-Amino-1-[2-(6-methoxy-quinazolin-4-yl)-ethyl]-cyclohexanol

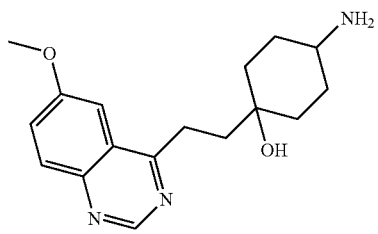

Ammonium acetate (14 g, 44 mmol) and sodium triacetoxyborohydride (1.2 g, 5 mmol) were added to a solution of 4-hydroxy-4-[2-(6-methoxy-quinazolin-4-yl)-ethyl]-cyclohexanone (1.25 g, 4.2 mmol) in methanol (50 ml). The reaction mixture was stirred overnight and concentrated to dryness by rotary evaporation. The residue was diluted with water (100 ml) and dichloromethane (100 ml), the phases were separated and the aqueous phase was extracted twice using 50 ml of dichloromethane each time. The combined organic phases were dried over $Na_2SO_4$, filtered and concentrated to dryness by rotary evaporation.

Yield: 0.85 g. 2.82 mmol (oil) cis/trans mixture MS (EI) m/z 302 $[M+H]^+$

11.b) 4-[(Benzo[1,2,5]thiadiazol-5-ylmethyl)-amino]-1-[2-(6-methoxy-quinazolin-4-yl)-ethyl]-cyclohexanol

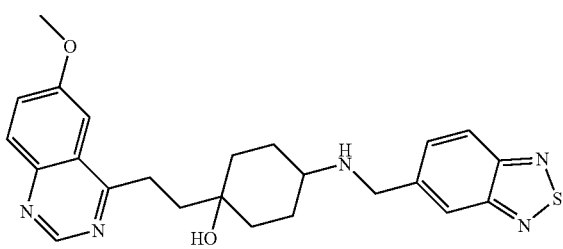

Molecular sieve, type 3A, (1 g) and benzo[1,2,5]thiadiazol-5-carbaldehyde (0.066 g, 0.4 mmol) were added to a solution of 4-amino-1-[2-(6-methoxy-quinazolin-4-yl)-ethyl]-cyclohexanol (0.116 g, 0.38 mmol) in methanol (1 ml) and dichloroethane (3 ml). The reaction mixture was stirred at room temperature for 20 hours and sodium triacetoxyborohydride (0.22 g, 1.04 mmol) was added. The reaction mixture was stirred at room temperature for 2 hours and then filtered over Hydromatrix (wetted with an $NaHCO_3$ solution, 2 ml) and subsequently washed with dichloromethane. The filtrate was concentrated to dryness by rotary evaporation. The residue was purified by column chromatography on silica gel (dichloromethane/MeOH 9/1 1% $NH_4OH$).

Yield: 0.112 g. 0.24 mmol (oil) cis/trans-mixture. MS (EI) m/z 450 $[M+H]^+$

Example 12

1-[2-(6-Methoxy-quinazolin-4-yl)-ethyl]-4-(3-phenyl-allylamino)-cyclohexanol

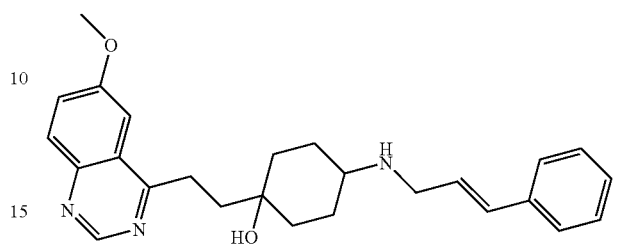

In an analogous manner, starting from 4-amino-1-[2-(6-methoxy-quinazolin-4-yl)-ethyl]-cyclohexanol (Example 11.b), 1-[2-(6-methoxy-quinazolin-4-yl)-ethyl]-4-(3-phenyl-allylamino)-cyclohexanol in the form of a cis/trans mixture was produced in a yield of 54% (MS (EI) m/z 418 $[M+H]^+$).

Example 13

4-(3-Furan-2-yl-allylamino)-1-[2-(6-methoxyquinazolin-4-yl)-ethyl]-cyclohexanol

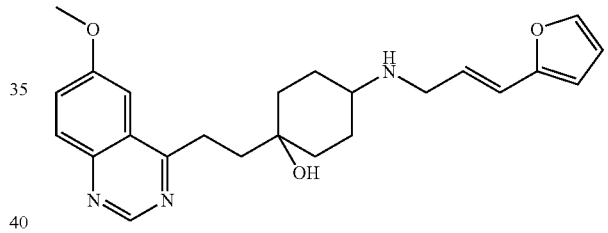

In an analogous manner, starting from 4-amino-1-[2-(6-methoxy-quinazolin-4-yl)-ethyl]-cyclohexanol (Example 11.b), 4-(3-furan-2-yl-allylamino)-1-[2-(6-methoxy-quinazolin-4-yl)-ethyl]-cyclohexanol in the form of a cis/trans mixture was produced in a yield of 62% (MS (EI) m/z 408 $[M+H]^+$).

Example 14

4-[(2,3-Dihydro-benzo[1,4]dioxin-6-ylmethyl)amino]-1-[2-(6-methoxy-quinazolin-4-yl)-ethyl]-cyclohexanol

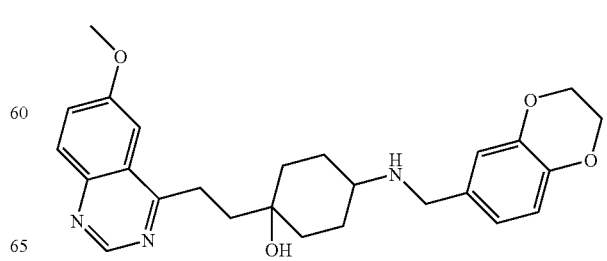

In an analogous manner, starting from 4-amino-1-[2-(6-methoxy-quinazolin-4-yl)-ethyl]-cyclohexanol (Example 11.b), 4-[(2,3-dihydro-benzo[1,4]dioxin-6-ylmethyl)-amino]-1-[2-(6-methoxy-quinazolin-4-yl)-ethyl]-cyclohexanol in the form of a cis/trans mixture was produced in a yield of 68% (MS (EI) m/z 450 [M+H]⁺).

Example 15

1-[2-(6-Methoxy-quinazolin-4-yl)-ethyl]-4-[(quinoxalin-2-ylmethyl)-amino]-cyclohexanol

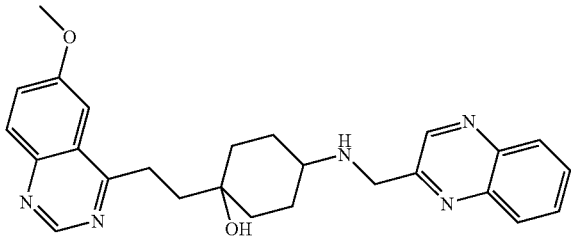

In an analogous manner, starting from 4-amino-1-[2-(6-methoxy-quinazolin-4-yl)-ethyl]-cyclohexanol (Example 11.b), 1-[2-(6-methoxy-quinazolin-4-yl)-ethyl]-4-[(quinoxalin-2-ylmethyl)-amino]-cyclohexanol in the form of a cis/trans mixture was produced in a yield of 59% (MS (EI) m/z 450 [M+H]⁺).

Example 16 cis- and trans-4-[(Benzo[1,3]dioxol-5-ylmethyl)-amino]-1-[2-(6-methoxy-[1,5]naphthyridin-4-yl)ethyl]-cyclohexanol 16 a) 8-(6-Methoxy-[1,5]naphthyridin-4-ylethynyl)-1,4-dioxa-spiro[4.5]decan-8-ol

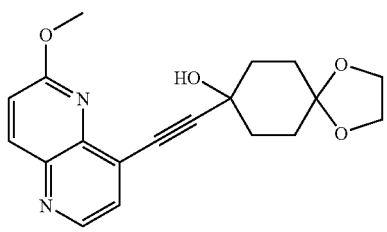

A degassed solution of trifluoromethanesulphonic acid 6-methoxy-[1,5]naphthyridin-4-yl ester (986 mg, 3.2 mmol) (WO 03 010138) and 8-ethynyl-1,4-dioxa-spiro[4.5]decan-8-ol (638 mg, 3.5 mmol) (prepared according to J. Chem. Soc. Perk. Trans. 1, 2000, 3382) in DMF (3 ml) was added dropwise to a likewise degassed suspension of copper(I) iodide (50 mg) and PdCl₂(PPh₃)₂ (100 mg) in DMF (2 ml) and triethylamine (3 ml). The reaction mixture was stirred at room temperature for 30 minutes and diluted with water and ether, and the organic phase was washed with water, saturated ammonium chloride solution and saturated sodium chloride solution, dried over MgSO₄ and concentrated. The crude product was purified by chromatography on silica gel (hex/EtOAc 1:1, EtOAc).

Yield: 0.965 g, 2.8 mmol (oil). MS (EI) m/z 341 [M+H]⁺

16.b) 8-[2-(6-Methoxy-[1,5]naphthyridin-4-yl)-ethyl]-1,4-dioxa-spiro[4.5]decan-8-ol

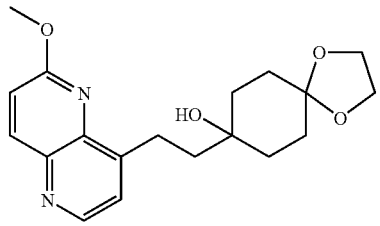

A solution of 8-(6-methoxy-[1,5]naphthyridin-4-ylethynyl)-1,4-dioxa-spiro[4.5]decan-8-ol (965 mg, 2.8 mmol) in ethanol (100 ml) was hydrogenated for 6 hours over PtO₂ (200 mg) at 1 bar of hydrogen. The catalyst was filtered off and replaced by fresh catalyst and the hydrogenation was continued for a further 3 hours. The catalyst was filtered off and the solvent was concentrated. The crude product was purified by chromatography on silica gel (EtOAc).

Yield: 0.960 g, 2.79 mol (oil). MS (EI) m/z 334.4 [M+H]⁺

16.c) 4-Hydroxy-4-[2-(6-methoxy-[1,5]naphthyridin-4-yl)ethyl]-cyclohexanone

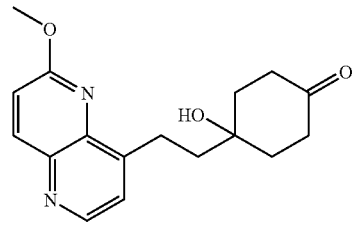

A solution of 8-[2-(6-methoxy-[1,5]naphthyridin-4-yl)ethyl]-1,4-dioxa-spiro[4.5]decan-8-ol (960 mg, 2.79 mmol) in THF/H₂O/AcOH (2:2:3, 22 ml) was stirred overnight at 65° C. The reaction mixture was concentrated and purified by chromatography on silica gel (EtOAc).

Yield: 0.700 g, 2.33 mmol (oil). MS (EI) m/z 301 [M+H]⁺

16.d) cis- and trans-4-[(Benzo[1,3]dioxol-5-ylmethyl)amino]-1-[2-(6-methoxy-[1,5]naphthyridin-4-yl)-ethyl]-cyclohexanol

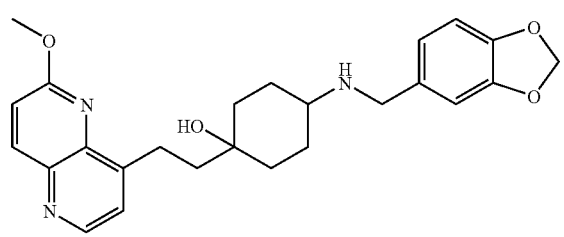

NaBH(OAc)₃ (100 mg) was added to a solution of 4-hydroxy-4-[2-(6-methoxy-[1,5]naphthyridin-4-yl)-ethyl]-cyclohexanone (100 mg, 0.3 mmol) and piperonylamine (100 µl) in THF (3 ml). The reaction mixture was stirred at room temperature for 4 hours, and diluted with dichloromethane and ammonium hydroxide. The organic phase was dried over MgSO₄ and concentrated. The residue was purified by chromatography on silica gel (EtOAc/MeOH 9:1+1% NH₄OH). cis-4-[(Benzo[1,3]dioxol-5-ylmethyl)-amino]-1-[2-(6-methoxy-[1,5]naphthyridin-4-yl)-ethyl]-cyclohexanol (38 mg, MS (EI) m/z 357 [M+H]⁺) and trans-4-[(benzo-[1,3]dioxol-5-ylmethyl)-amino]-1-[2-(6-methoxy-[1,5]-naphthyridin-4-yl)-ethyl]-cyclohexanol (63 mg, MS (EI) m/z 357 [M+H]⁺) were obtained.

Example 17 cis- and trans-4-[(Benzo[1,3]dioxo-5-ylmethyl)-amino]-1-[2-(6-methoxy-[1,5]naphthyridin-4-yl)ethyl]-cyclohexanol 17.a) 4-[2-(6-Ethoxy-quinolin-4-yl)-ethyl]-4-hydroxy-cyclohexanone

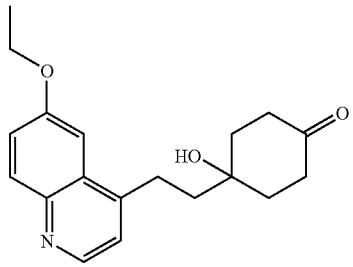

In a manner analogous to Example 16.c, 4-[2-(6-ethoxy-quinolin-4-yl)-ethyl]-4-hydroxy-cyclohexanone was prepared from 6-ethoxy-quinolin-4-ol. MS (EI) m/z 314 [M+H]⁺)

6-Ethoxyquinolin-4-ol has already been described in Synth. Comm. 2002, 32, 3185.

17.b) cis- and trans-4-[(Benzo[1,3]dioxo-5-ylmethyl)-amino]-1-[2-(6-methoxy-[1,5]naphthyridin-4-yl)-ethyl]-cyclohexanol

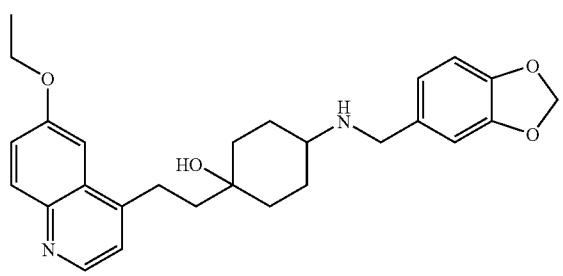

In a manner analogous to Example 16.d, there were obtained cis-4-[(benzo[1,3]dioxol-5-ylmethyl)-amino]-1-[2-(6-methoxy[1,5]naphthyridin-4-yl)-ethyl]-cyclohexanol (48% yield, MS (EI) m/z 449 [M+H]⁺) and trans-4-[(benzo[1,3]-dioxol-5-ylmethyl)-amino]-1-[2-(6-methoxy-[1,5]naphthyridin-4-yl)-ethyl]-cyclohexanol (29% yield, MS (EI) m/z 449 [M+H]⁺).

Example 18

Synthesis of cis- and trans-4-[(2,3-dihydro-benzo[1,4]dioxin-6-ylmethyl)-amino]-1-[2-(6-methoxy-[1,5]-naphthyridin-4-yl)-ethyl]-cyclohexanol 18.a) 4-Amino-1-[2-(6-methoxy-[1,5]naphthyridin-4-yl)-ethyl]-cyclohexanol

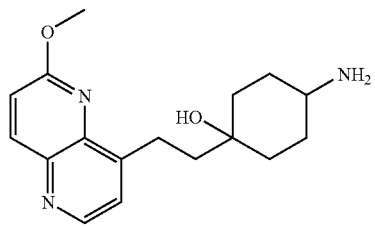

Sodium triacetoxyborohydride (1.89 g, 8.75 mmol) was added to a solution of 4-hydroxy-4-[2-(6-methoxy-[1,5]naphthyridin-4-yl)-ethyl]-cyclohexanone (3 g, 8.5 mmol) and ammonium acetate (25.5 g) in methanol (65 ml). The reaction mixture was stirred at room temperature for 3 hours, 0.5 g of sodium triacetoxyborohydride was added and stirring was continued for a further 2 hours. The reaction mixture was diluted with NH₄OH and extracted with EtOAc and dichloromethane. Organic phases were dried over MgSO₄ and concentrated.

Yield: 2.6 g, (oil), cis/trans mixture MS (EI) m/z 302 [M+H]⁺

18.b) cis- and trans-4-[(2,3-Dihydro-benzo[1,4]dioxin-6-ylmethyl)-amino]-1-[2-(6-methoxy-[1,5]naphthyridin-4-yl)ethyl]-cyclohexanol

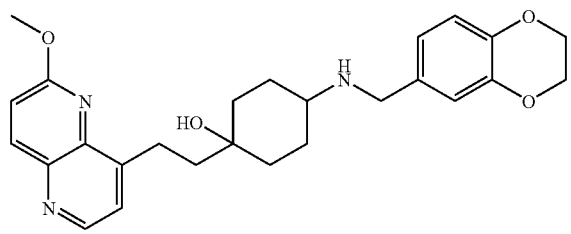

Molecular sieve, type 3A, (2.5 g) was added to a solution of 4-amino-1-[2-(6-methoxy-[1,5]naphthyridin-4-yl)-ethyl]-cyclohexanol (1250 mg, 4.14 mmol) and 2,3-dihydro-benzo[1,4]dioxin-6-carbaldehyde (680 mg, 4.14 mmol) in methanol (25 ml) and THF (25 ml). The reaction mixture was stirred at room temperature for 20 hours and sodium borohydride (157 mg, 4.14 mmol) was added. The reaction mixture was stirred at room temperature for 1 hour and then filtered over Hydromatrix (wetted with NH₄OH) and subsequently washed with dichloromethane. The filtrate was concentrated to dryness by rotary evaporation. The residue was purified by column chromatography on silica gel (EtOAc/MeOH 9/1, 1% NH₄OH).

cis-4-[(2,3-Dihydro-benzo[1,4]dioxin-6-ylmethyl)-amino]-1-[2-(6-methoxy-[1,5]naphthyridin-4-yl)-ethyl]-cyclohexanol (640 mg, 34%, MS (EI) m/z 450 [M+H]⁺) and trans-4-[(2,3-dihydro-benzo[1,4]dioxin-6-ylmethyl)-amino]-1-[2-(6-methoxy-[1,5]naphthyridin-4-yl)-ethyl]-cyclohexanol (360 mg, 19%, MS (EI) m/z 450 [M+H]⁺) were obtained.

Example 19 cis- and trans-6-({4-Hydroxy-4-[2-(6-methoxy-[1,5] naphthyridin-4-yl)-ethyl]-cyclohexylamino}-methyl)-4H-benzo[1,4]oxazin-3-one

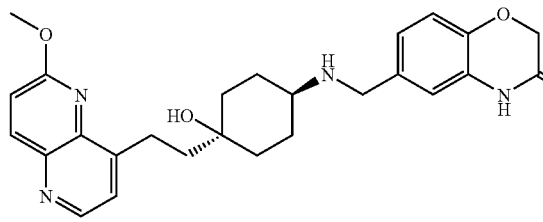

Starting from 4-amino-1-[2-(6-methoxy-[1,5]naphthyridin-4-yl)-ethyl]-cyclohexanol and 3-oxo-3,4-dihydro-2H-benzo-[1,4]oxazine-6-carbaldehyde, there were obtained, in a manner analogous to Example 18, cis-6-({4-hydroxy-4-[2-(6-methoxy-[1,5]naphthyridin-4-yl)-ethyl]-cyclohexylamino}-methyl)-4H-benzo[1,4]oxazin-3-one (330 mg, 17%, MS (EI) m/z 464 [M+H]+) and trans-6-({4-hydroxy-4-[2-(6-methoxy-[1,5]naphthyridin-4-yl)-ethyl]-cyclohexylamino}-methyl)-4H-benzo[1,4]oxazin-3-one (980 mg, 44%, MS (EI) m/z 464 [M+H]+).

Example 20 cis- and trans-4-[(2,3-Dihydro-benzo[1,4]-dioxin-6-ylmethyl)-amino]-1-[2-(6-methoxy-quinolin-4-yl) ethyl]-cyclohexanol 20.a) 4-Amino-1-[2-(6-methoxy-quinolin-4-yl)-ethyl]-cyclohexanol

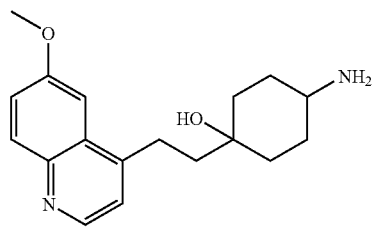

4-Amino-1-[2-(6-methoxy-quinolin-4-yl)-ethyl]-cyclohexanol was obtained analogously to the sequence of Examples 14 and 15 starting from trifluoromethanesulphonic acid 6-methoxy-quinolin-4-yl ester and 8-ethenyl-1,4-dioxa-spiro[4.5]decan-8-ol.

20.b) 4-[(2,3-Dihydro-benzo[1,4]dioxin-6-ylmethyl)-amino]-1-[2-(6-methoxy-quinolin-4-yl)-ethyl]-cyclohexanol

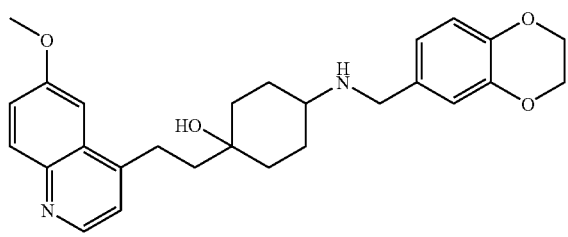

Starting from 4-amino-1-[2-(6-methoxy-quinolin-4-yl) ethyl]-cyclohexanol and 2,3-dihydro-benzo[1,4]dioxin-6-carbaldehyde, there were obtained, in analogy to Example 18, cis-4-[(2,3-dihydrobenzo[1,4]dioxin-6-yl-methyl)-amino]-1-[2-(6-methoxy-quinolin-4-yl)-ethyl]-cyclohexanol (50 mg, MS (EI) m/z 449.5 [M+H]+) and trans-4-[(2,3-dihydro-benzo[1,4]dioxin-6-ylmethyl)-amino]-1-[2-(6-methoxy-quinolin-4-yl)-ethyl]-cyclohexanol (56 mg, MS (EI) m/z 449.5 [M+H]+).

Example 21 cis- and trans-6-({4-Hydroxy-4-[2-(6-methoxy-quinolin-4-yl)-ethyl]-cyclohexylamino}-methyl)-4H-benzo-[1,4]oxazin-3-one

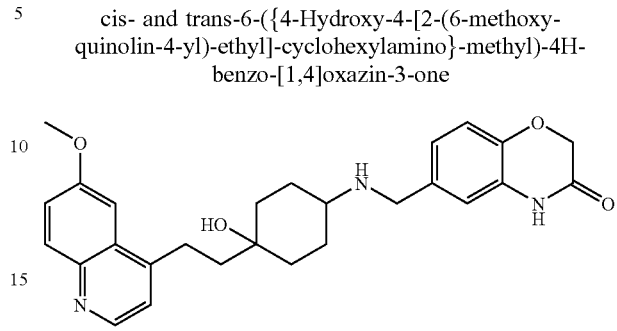

Starting from 4-amino-1-[2-(6-methoxy-quinolin-4-yl) ethyl]-cyclohexanol and 3-oxo-3,4-dihydro-2H-benzo[1,4]-oxazine-6-carbaldehyde, there were obtained, in analogy to Example 18, cis-6-({4-hydroxy-4-[2-(6-methoxy-quinolin-4-yl)-ethyl]-cyclohexylamino}-methyl)-4H-benzo[1,4]oxazin-3-one (32 mg, MS (EI) m/z 462.6 [M+H]+) and trans-6-({4-hydroxy-4-[2-(6-methoxy-quinolin-4-yl)-ethyl]-cyclohexyl-amino}-methyl)-4H-benzo[1,4]oxazin-3-one (40 mg, MS (EI) m/z 462.6 [M+H]+).

Example 22

4-[(2,3-Dihydro-[1,4]dioxino[2,3-c]pyridin-7-ylmethyl)-amino]-1-[2-(6-methoxy-quinolin-4-yl)-ethyl]-cyclohexanol

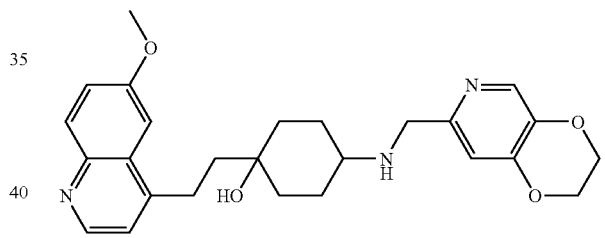

In analogy to Example 11.b, 4-[(2,3-dihydro-[1,4]dioxino[2,3-c]pyridin-7-ylmethyl)-amino]-1-[2-(6-methoxyquinolin-4-yl)-ethyl]-cyclohexanol was obtained in a yield of 72% in the form of a cis/trans mixture (MS (EI) m/z 450 [M+H]+).

2,3-Dihydro-[1,4]dioxino[2,3-c]pyridine-7-carbaldehyde was prepared according to WO 03/010138.

Example 23

4-[(Benzo[1,2,5]thiadiazol-5-ylmethyl)-amino]-1-[2-(6-methoxy-quinolin-4-yl)-ethyl]-cyclohexanol

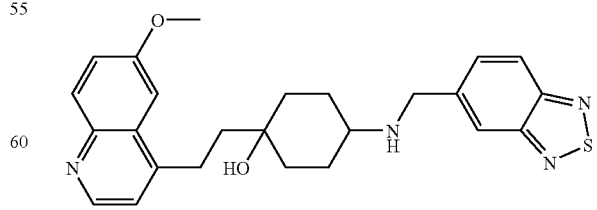

In analogy to Example 11.b, 4-[(benzo[1,2,5]thiadiazol-5-ylmethyl)-amino]-1-[2-(6-methoxy-quinolin-4-yl)-ethyl]-cyclohexanol was obtained in a yield of 47% in the form of a cis/trans mixture (MS (EI) m/z 449 [M+H]+).

Example 24

1-[2-(6-Methoxy-quinolin-4-yl)-ethyl]-4-(3-phenyl-allylamino)-cyclohexanol

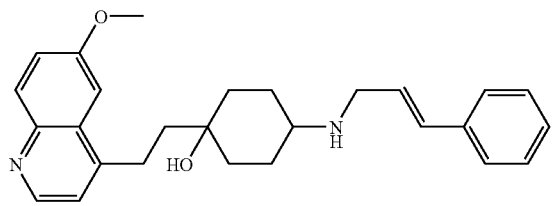

In analogy to Example 11.b, 1-[2-(6-methoxy-quinolin-4-yl)-ethyl]-4-(3-phenyl-allylamino)-cyclohexanol was obtained in a yield of 46% in the form of a cis/trans mixture (MS (EI) m/z 418[M+H]$^+$).

Example 25

1-[2-(6-Methoxy-quinolin-4-yl)-ethyl]-4-[(quinoxalin-2-ylmethyl)-amino]-cyclohexanol

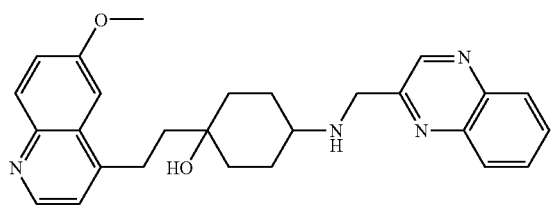

In analogy to Example 11.b, 1-[2-(6-methoxy-quinolin-4-yl)-ethyl]-4-[(quinoxalin-2-ylmethyl)-amino]-cyclohexanol was obtained in a yield of 61% in the form of a cis/trans mixture (MS (EI) m/z 443[M+H]$^+$).

Example 26

6-({4-Hydroxy-4-[2-(6-methoxy-quinolin-4-yl) ethyl]-cyclohexylamino}-methyl)-2,3-dihydro-benzo[1,4]-dioxin-5-ol

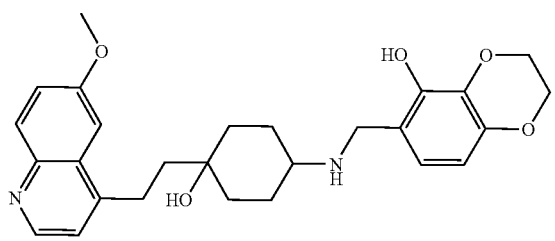

In analogy to Example 11.b, 6-({4-hydroxy-4-[2-(6-methoxy-quinolin-4-yl)-ethyl]-cyclohexylamino}-methyl)-2,3-dihydro-benzo[1,4]dioxin-5-ol was obtained in a yield of 19% in the form of a cis/trans mixture (MS (EI) m/z 465[M+H]$^+$).

The corresponding aldehyde was prepared analogously to J. heterocycl. Chem 1989, 26, 193–197.

Example 27

4-[(2-Chloro-quinolin-3-ylmethyl)-amino]-1-[2-(6-methoxy-quinolin-4-yl)-ethyl]-cyclohexanol

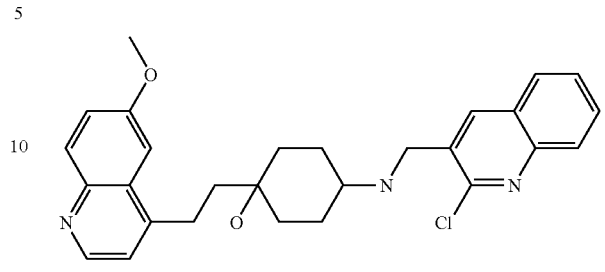

In analogy to Example 11.b, 4-[(2-chloro-quinolin-3-ylmethyl)-amino]-1-[2-(6-methoxy-quinolin-4-yl)-ethyl]-cyclohexanol was obtained in a yield of 56% in the form of a cis/trans mixture (MS (EI) m/z 477[M+H]$^+$).

Example 28

Synthesis of 2-{4-hydroxy-4-[2-(6-methoxy-quinolin-4-yl)-ethyl]-cyclohexylamino}-N-pyridin-2-yl-acetamide

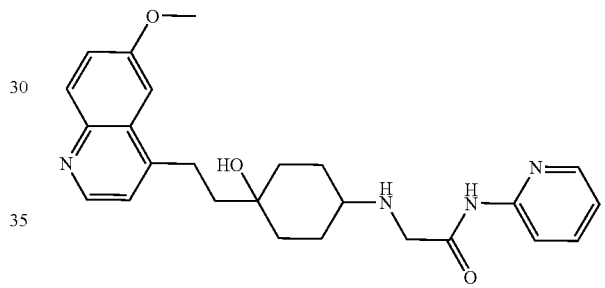

2-Bromo-N-pyridin-2-yl-acetamide (0.068 g, 0.31 mmol) and potassium carbonate (0.045 g, 0.34 mmol) were added to a solution of 4-amino-1-[2-(6-methoxy-quinolin-4-yl)-ethyl]-cyclohexanol (0.094 g, 0.31 mmol) in DMF (3.5 ml). The reaction mixture was stirred at room temperature for 2 days and then concentrated to dryness by rotary evaporation. The residue was purified by column chromatography on silica gel (dichloromethane/MeOH 19/1 1% ammonium hydroxide).

Yield: 0.11 g (0.25 mmol) in the form of a cis/trans mixture. MS (EI) m/z 435 [M+H]$^+$ 2-Bromo-N-pyridin-2-yl-acetamide has already been described in WO 02/24684.

Example 29

Benzo[1,3]dioxol-5-ylmethyl-{4-[2-(6-methoxy-quinolin-4-yl)-ethyl]-cyclohexyl}-amine 29.a) 8-Ethynyl-1,4-dioxa-spiro[4.5]decane:

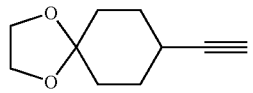

A solution of carbon tetrabromide (12.4 g, 37.4 mmol) in dichloromethane (40 ml) was added at –30° C. to a solution of triphenylphosphine (19.6 g, 74.6 mmol) and 1,4-dioxaspiro[4.5]dec-8-carbaldehyde (5 g, 29.37 mmol) in dichloromethane (100 ml). After the solution had been stirred at room temperature for 2 hours, it was concentrated to dryness by rotary evaporation. The residue was diluted with ethyl acetate and n-hexane (1:3; 500 ml), filtered over Celite and concentrated to dryness by rotary evaporation. The residue was purified by column chromatography on silica gel (hexane/EtOAc 4/1). Yield: 6.08 g (18.6 mmol). That material was dissolved in THF (90 ml) and, at −78° C., n-BuLi (16.5 ml, 38 mmol 2.3N in hexane) was added dropwise. After the solution had been stirred at −78° C. for 1 hour, a solution of 10% NaHSO$_4$ (50 ml) was added. The aqueous phase was extracted three times using 50 ml of ethyl acetate each time, dried over MgSO$_4$, filtered and concentrated to dryness by rotary evaporation. The residue was purified by column chromatography on silica gel (hexane/EtOAc 5/1).

Yield: 2.74 g (16.5 mmol) δ H (CDCl$_3$, 300 MHz): 1.61 (m, 2H); 1.70–1.94 (m, 6H); 2.07 (d, J=2.5 Hz, 1H); 2.51 (m, 1H); 3.96 (s, 4H).

29.b) 4-(1,4-Dioxaspiro[4.5]dec-8-ylethynyl)-6-methoxy-quinoline

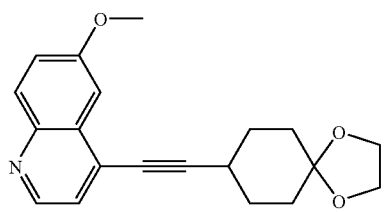

A degassed solution of trifluoromethanesulphonic acid 6-methoxyquinolin-4-yl ester (0.95 g, 3.1 mmol) and 4-(1,4-dioxa-spiro[4.5]dec-8-ylethynyl)-6-methoxy-quinoline (0.514 g, 3.1 mmol) in DMF (6 ml) and TEA (12 ml) was added to a mixture of PdCl$_2$(PPh$_3$)$_2$ (0.110 g, 0.157 mmol) and CuI (0.055 g, 0.288 mmol). After the solution had been stirred at room temperature for 1 hour, it was concentrated to dryness by rotary evaporation. The residue was purified by column chromatography on silica gel (EtOAc).

Yield: 0.83 g (2.56 mmol) MS (EI) m/z 324 [M+H]$^+$

29.c) 4-[2-(1,4-Dioxaspiro[4.5]dec-8-yl)ethyl]-6-methoxy-quinoline

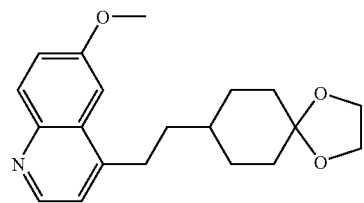

Platinum oxide ((0.462 g) was added to a solution of 4-(1,4-dioxa-spiro[4.5]dec-8-yl-ethynyl)-6-methoxy-quinoline (0.83 g, 2.53 mmol) in EtOH (30 ml) and ethyl acetate (10 ml) and hydrogenation was carried out under a hydrogen atmosphere (1 bar). The catalyst was filtered off and the filtrate was concentrated to dryness by rotary evaporation. The residue was purified by column chromatography on silica gel (EtOAc and then EtOAc/-methanol 9/1).

Yield: 0.77 g (2.35 mmol) MS (EI) m/z 328 [M+H]$^+$

29.d) 4-[2-(6-Methoxy-quinolin-4-yl)-ethyl]-cyclohexanone

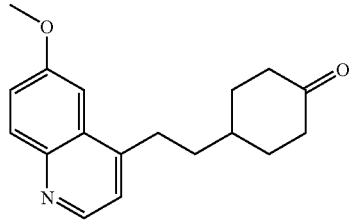

A solution of 4-[2-(1,4-dioxa-spiro[4.5]dec-8-yl)-ethyl]-6-methoxy-quinoline (0.77 g, 2.35 mmol) in AcOH/THF/H$_2$O (3/2/2, 10 ml) was stirred at 60° C. for 10 hours. The reaction mixture was concentrated to dryness by rotary evaporation. The residue was diluted with EtOAc (100 ml), washed with NaHCO$_3$ (100 ml), dried over MgSO$_4$, filtered and concentrated to dryness by rotary evaporation.

Yield: 0.631 g (2.23 mmol) MS (EI) m/z 284 [M+H]$^+$

29.e) Benzo[1,3]dioxol-5-ylmethyl-{4-[2-(6-methoxy-quinolin-4-yl)-ethyl]-cyclohexyl}-amine

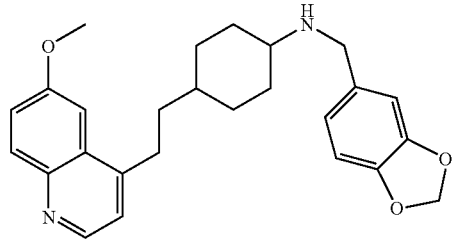

Piperonylamine (0.038 ml, 0.3 mmol) and sodium triacetoxyborohydride (0.05 g) were added to a solution of 4-[2-(6-methoxy-quinolin-4-yl)-ethyl]-cyclohexanone (0.05 g, 0.176 mmol) in dichloromethane (0.5 ml). The reaction mixture was stirred overnight and then filtered over Hydromatrix (wetted with an NaHCO$_3$ solution, 2 ml) and subsequently washed with dichloromethane. The filtrate was concentrated to dryness by rotary evaporation. The residue was purified by column chromatography on silica gel (EtOAc and then EtOAc:MeOH 9/1).

Yield: 0.069 g (0.165 mmol) in the form of a cis/trans mixture MS (EI) m/z 419 [M+H]$^+$

Example 30

6-({4-[2-(6-Methoxy-quinolin-4-yl)-ethyl]-cyclohexylamino}-methyl)-4H-benzo[1,4]oxazin-3-one

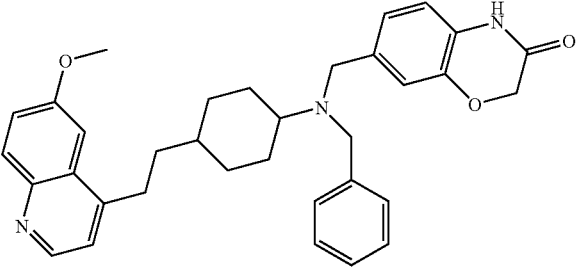

30.a) 7-[(Benzyl-{4-[2-(6-methoxy-quinolin-4-yl)-ethyl]-cyclohexyl}-amino)-methyl]-4H-benzo[1,4]oxazin-3-one Benzylamine (0.135 ml, 1.24 mmol) and sodium triacetoxyborohydride (0.315 g, 1.55 mmol) were added to a solution of 4-[2-(6-methoxy-quinolin-4-yl)-ethyl]-cyclohexanone (Example 26.e) (0.35 g, 1.23 mmol) in dichloroethane (8 ml). The reaction mixture was stirred for 2 hours. 3-Oxo-3,4-dihydro-2H-benzo[1,4]oxazine-6-carbaldehyde (0.230 g, 1.3 mmol), THF (4 ml and sodium triacetoxyborohydride (0.315 g, 1.55 mmol) was added. The reaction mixture was stirred overnight and then filtered over Hydromatrix (wetted with an NaHCO₃ solution, 10 ml) and subsequently washed with dichloromethane. The filtrate was concentrated to dryness by rotary evaporation. The residue was purified by column chromatography on silica gel (dichloromethane/MeOH 19/1).

Yield: 0.540 g (1.0 mmol) MS (EI) m/z 536 [M+H]⁺

30.b) 6-({4-[2-(6-Methoxy-quinolin-4-yl)-ethyl]-cyclohexylamino}-methyl)-4H-benzo[1,4]oxazin-3-one

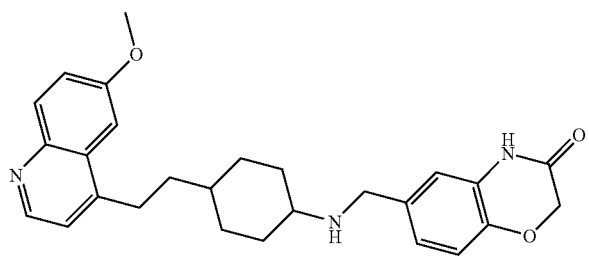

20% Pd(OH)₂ on carbon (0.5 g) was added to a solution of 7-[(benzyl-{4-[2-(6-methoxy-quinolin-4-yl)-ethyl]-cyclohexyl}-amino)-methyl]-4H-benzo[1,4]oxazin-3-one (0.535 g, 1 mmol) in THF (15 ml) and MeOH (5 ml) and hydrogenation was carried out under a hydrogen atmosphere (1 bar). The reaction mixture was filtered and the filtrate was concentrated. The residue was purified by column chromatography on silica gel (dichloromethane/MeOH 9/1 1% ammonium hydroxide).

Yield: 0.251 g (0.56 mmol) in the form of a cis/trans mixture MS (EI) m/z 446 [M+H]⁺

Example 31

2-{3-[(2,3-Dihydro-benzo[1,4]dioxin-6-yl-methyl)amino]pyrrolidin-1-yl}-1-(6-methoxy-quinolin-4-yl)-ethanol 31.a) Benzyl (3RS)-[(2,3-dihydro-benzo[1,4]dioxin-6-ylmethyl)-amino]-pyrrolidine-1-carbamate

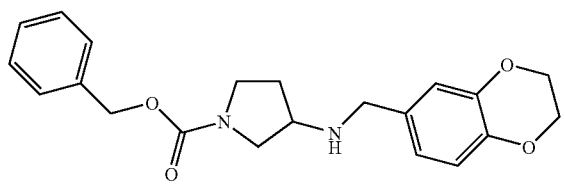

Sodium bicarbonate (7 g) and chloroformic acid benzyl ester (2.8 ml) were added at 0° C. to a solution of 3-aminopyrrolidine dihydrochloride (3.2 g, 20.1 mmol) in water (100 ml) and acetone (150 ml). The reaction mixture was stirred for 10 hours and then concentrated to dryness by rotary evaporation. The residue was diluted with EtOAc (100 ml). The two phases were separated and the aqueous phase was extracted twice using 50 ml of EtOAc each time. The combined organic phases were washed with 20 ml of saturated sodium chloride solution, dried over MgSO₄, filtered and concentrated to dryness by rotary evaporation. The residue was dissolved in dichloromethane (30 ml), and 1,4-benzodioxane-6-carbaldehyde (1.6 g) and, after 20 minutes, sodium triacetoxyborohydride (4 g) were added. The reaction mixture was stirred overnight and then diluted with sodium bicarbonate (80 ml). The two phases were separated and the aqueous phase was extracted twice using 50 ml of dichloromethane each time. The combined organic phases were washed with 20 ml of saturated sodium chloride solution, dried over MgSO₄, filtered and concentrated to dryness by rotary evaporation. The residue was purified by column chromatography on silica gel (EtOAc:MeOH 9/1).

Yield: 3.75 g (10.1 mmol) δ H (CDCl₃, 300 MHz): 1.57 (br s, 1H), 1.77 (m, 1H), 2.07 (m, 1H); 3.21 (m, 1H); 3.37 (m, 2H); 3.61 (m, 2H), 3.70 (s, 2H); 4.25 (s, 4H); 5.14 (s, 2H); 6.76–6.84 (m, 3H); 7.30–7.38 (m, 5H).

31.b) (2,3-Dihydro-benzo[1,4]dioxin-6-ylmethyl)pyrrolidin-(3RS)-yl-amine

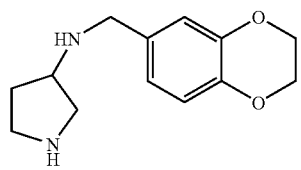

20% Pd(OH)₂ on carbon (1 g) was added to a solution of benzyl 3-[(2,3-dihydro-benzo[1,4]dioxin-6-yl-methyl)-amino]pyrrolidin-1-carbamate (3.75 g, 10.1 mmol) in EtOH (20 ml) and EtOAc (20 ml) and hydrogenation was carried out under a hydrogen atmosphere (1 bar). The reaction mixture was filtered and the filtrate was concentrated.

Yield: 2.15 g (9.2 mmol) MS (EI) m/z 235 [M+H]⁺

31.c) 2-{(3RS)-[(2,3-Dihydro-benzo[1,4]dioxin-6-ylmethyl)-amino]-pyrrolidin-1-yl}-(1RS)-(6-methoxy-quinolin-4-yl)-ethanol

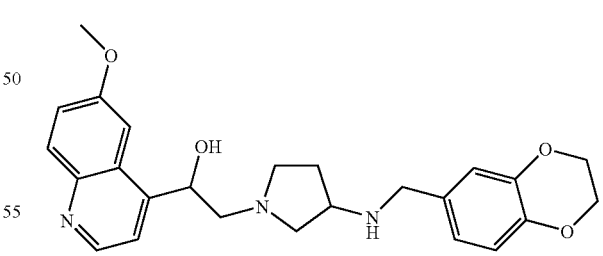

A solution of 6-methoxy-4-oxiranylquinoline (0.201 g, 1 mmol) and (2,3-dihydrobenzo[1,4]dioxin-6-ylmethyl)-pyrrolidin-3-ylamine (0.234 g, 1 mmol) in ethanol (2 ml) was heated at 80° C. for 16 hours. The reaction mixture was cooled to room temperature and concentrated to dryness by rotary evaporation. The residue was purified by column chromatography on silica gel (EtOAc and then EtOAc/MeOH 5:1).

Yield: 0.208 g (0.477 mmol) MS (EI) m/z 436.5 [M+H]⁺

Example 32

4-(4-Methoxy-benzylamino)-1-[2-(6-methoxy-quinazolin-4-yl)-ethyl]cyclohexanol

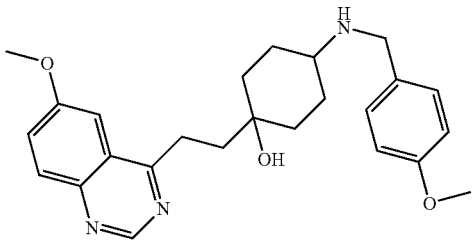

4-Methoxybenzylamine (0.026 ml, 0.24 mmol) and then sodium triacetoxyborohydride (0.08 g, 0.377 mmol) were added to a solution of 4-hydroxy-4-[2-(6-methoxyquinazolin-4-yl)-ethyl]cyclohexanone (0.06 g, 0.2 mmol) in dichloromethane (1 ml). The reaction mixture was stirred overnight and then filtered over Hydromatrix (wetted with an NaHCO₃ solution, 2 ml) and subsequently washed with dichloromethane. The filtrate was concentrated to dryness by rotary evaporation. The residue was purified by column chromatography on silica gel (dichloromethane/MeOH 9/1 and then dichloromethane/MeOH 9/1 and 2% triethylamine).

Yield: 0.052 g (0.124 mmol) in the form of a cis/trans mixture MS (EI) m/z 422 [M+H]⁺

Example 33

4-(3-Fluorobenzylamino)-1-[2-(6-methoxy-quinazolin-4-yl)-ethyl]cyclohexanol

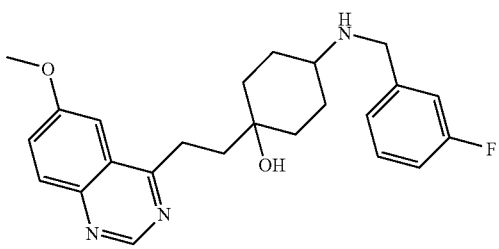

The compound was prepared analogously to Example 10, starting from 3-fluorobenzylamine (0.026 ml, 0.24 mmol).

Yield: (0.052 g, 0.124 mmol) in the form of a cis/trans mixture MS (EI) m/z 410 [M+H]⁺

Example 34

2-{4-[(2,3-Dihydrobenzo[1,4]dioxin-6-yl-ethyl)-amino]-azepan-1-yl}-1-(6-methoxy-quinolin-4-yl) ethanol

34.a) tert-Butyl 4-oxoazepane 1-carbamate

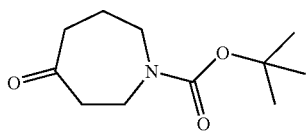

A mixture of 5-oxoazepane-1,4-dicarboxylic acid 1-tert-butyl ester 4-ethyl ester (5.7 g, 20 mmol; prepared as described in Synthetic Communications 1992, 22, 1249) was refluxed for 3 hours in a mixture of 3N NaOH (50 ml) and THF (25 ml). The reaction mixture was cooled and neutralised with dilute HCl. The mixture was extracted with ethyl acetate and the organic phases were dried over MgSO₄ and concentrated.

Yield: 4.2 g (100%) ¹H-NMR (CDCl₃, 300 MHz): 1.46 (s, 9H); 1.80 (br, 2H); 2.60–2.7 (m, 4H); 3.4–3.6 (m, 4H).

34.b) tert-Butyl (4RS)-aminoazepane-1-carbamate

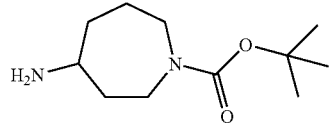

Ammonium acetate (3.5 g) and sodium cyanoborohydride (295 mg, 1 eq.) were added to a solution of tert-butyl 4-oxoazepane-1-carbamate (1 g, 4.68 mmol) in methanol (50 ml). The mixture was stirred overnight at room temperature. The reaction mixture was concentrated and the residue was dissolved in saturated potassium carbonate solution and ethyl acetate. The aqueous phase was extracted with ethyl acetate (2×50 ml), and the combined organic phases were dried over magnesium sulphate and concentrated. 1 g (100%) of product was obtained, which was further used without purification.

¹H-NMR (CDCl₃, 300 MHz): 1.46 (s, 9H); 1.5–1.75 (m, 2H); 1.8–2.05 (m, 4H); 2.4 (br, 2H); 2.95–3.05 (m, 1H); 3.1–3.6 (m, 4H). MS (EI) m/z 215.6 [M+H]⁺

34.c) tert-Butyl (4RS)-[(2,3-dihydrobenzo[1,4]dioxin-6-ylmethyl)-amino]-azepane-1-carbamate

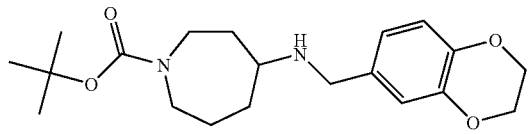

Acetic acid (500 µl) and sodium cyanoborohydride (126 mg) were added to a solution of tert-butyl 4-aminoazepane-1-carbamate (428 mg, 2 mmol) and 2,3-dihydrobenzo[1,4]-dioxin-6-carbaldehyde (330 µl, 2 mmol) in dichloroethane (10 ml). The mixture was stirred overnight at room temperature, diluted with saturated potassium carbonate solution and extracted with dichloromethane. The organic phases were dried over magnesium sulphate and concentrated. The product was purified by chromatography on silica gel (ethyl acetate).

Yield: 370 mg (51%)

¹H-NMR (CDCl₃, 300 MHz): 1.46 (s, 9H); 1.5–1.75 (m, 2H); 1.8–2.05 (m, 4H); 2.65 (m, 1H); 3.1–3.6 (m, 4H); 3.70 (s, 2H); 4.26 (s, 4H); 6.8–6.9 (m, 3H). MS (EI) m/z 363.6 [M+H]⁺

34.d) Azepan-(4RS)-yl-(2,3-dihydrobenzo[1,4]dioxin-6-ylmethyl)-amine

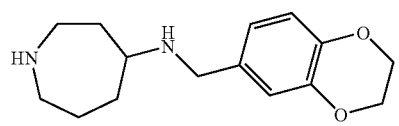

tert-Butyl 4-[(2,3-dihydrobenzo[1,4]dioxin-6-ylmethyl)-amino]-azepane-1-carbamate (370 mg, 1 mmol) was dissolved in a mixture of 10 ml of water and 2 ml of conc. HCl and stirred at room temperature for 24 hours. The reaction mixture was neutralised with solid potassium carbonate and extracted with ethyl acetate. Chromatography on silica gel (dichloromethane/MeOH 9:1) yielded 220 mg of pure product (85%).

¹H-NMR (CDCl₃, 300 MHz): 1.8–2.0 (m, 1H); 2.0–2.3 (m, 4H); 2.3–2.6 (m, 2H); 3.2–3.4 (m, 4H); 3.6–6.7 (m, 1H); 3.95 (dd, 2H); 4.2–4.3 (m, 5H); 6.8–7.1 (m, 3H). MS (EI) m/z 263.4 [M+H]⁺

34.e) 2-{(4RS)-[(2,3-Dihydrobenzo[1,4]dioxin-6-ylmethyl)amino]-azepan-1-yl}-(1RS)-(6-methoxy-quinolin-4-yl)ethanol

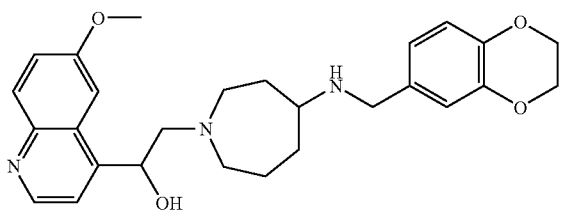

A mixture of azepan-4-yl-(2,3-dihydro-benzo[1,4]-dioxin-6-ylmethyl)amine (60 mg), 6-methoxy-4-oxiranylquinoline (50 mg), lithium perchlorate (25 mg) and potassium carbonate (35 mg) was heated overnight at 80° C. in DMF (1 ml). The reaction mixture was purified by chromatography on silica gel (dichloromethane/MeOH 9:1 (+2% NEt₃).

¹H-NMR (CDCl₃, 300 MHz): 1.5–2.0 (m, 7H); 2.45 (dd, 1H); 2.55–3.05 (m, 8H); 3.5–3.8 (m, 2H); 3.85 (s, 3H); 4.15 (s, 4H); 5.25–5.35 (m, 1H); 6.6–6.8 (m, 2H); 7.11 (dd, 1H); 7.30 (dd, 1H); 7.55 (dd, 1H); 7.97 (d, 1H); 8.7 (d, 1H). MS (EI) m/z 464.6 [M+H]⁺

Example 35

[1-(2,3-Dihydro-benzo[1,4]dioxin-6-yl-methyl)-azepan-4-yl](6-methoxyguinolin-4-ylmethyl)amine 35.a) tert-Butyl (4RS)-[(6-methoxy-quinolin-4-ylmethyl)-amino]-azepane-1-carbamate

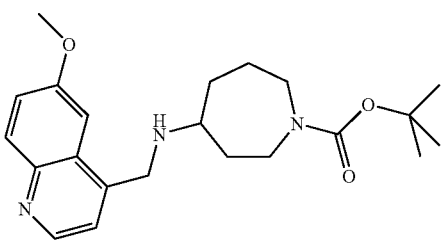

Sodium cyanoborohydride (170 mg, 2.7 mmol) was added to a solution of tert-butyl 4-aminoazepane-1-carbamate (568 mg, 2.65 mmol) and 6-methoxy-quinoline-4-carbaldehyde (497 mg (2.7 mmol) in dichloroethane (10 ml) and acetic acid (1 ml). The reaction mixture was stirred at room temperature overnight, poured onto saturated sodium carbonate solution and extracted with dichloromethane. The organic phase was dried over magnesium sulphate and concentrated. The product was purified by chromatography on silica gel (ethyl acetate).

Yield: 515 mg (51%) ¹H-NMR (CDCl₃, 300 MHz): 1.47 (s, 9H); 1.5–2.0 (m, 8H); 2.8–2.9 (m, 1H); 3.2–3.65 (m, 5H); 3.97 (s, 3H); 4.22 (s, 2H); 5.25–5.35 (m, 1H); 6.6–6.8 (m, 2H); 7.11 (dd, 1H); 7.35–7.45 (m, 3H); 8.02 (d, J=9.2 Hz, 1H); 8.73 (d, J=1.4 Hz, 1H). MS (EI) m/z 386.5 [M+H]⁺

35.b) Azepan-(4RS)-yl-(6-methoxy-quinolin-4-ylmethyl)amine

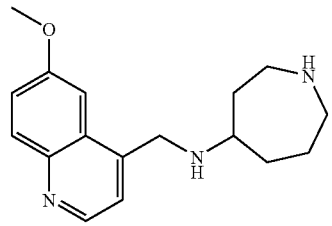

TFA (1 ml) was added at room temperature to a solution of tert-butyl 4-[(6-methoxy-quinolin-4-ylmethyl)amino]-azepane-1-carbamate (700 mg, 1.8 mmol) in dichloromethane (1 ml). The reaction mixture was stirred at room temperature for 3 hours, concentrated and taken up in aqueous NaOH. The aqueous phase was extracted with ethyl acetate and the combined organic phases were dried over sodium sulphate. The product was purified by chromatography on silica gel (DCM/MeOH 9:1 (1% NH₄OH)).

Yield: 477 mg (92%)

¹H-NMR (CDCl₃, 300 MHz): 1.7–2.3 (m, 6H); 3.0–3.3 (m, 4H); 3.35–3.45 (m, 1H); 3.97 (s, 3H); 4.2 (s, 2H); 7.28 (d, 1H); 7.35–7.45 (m, 2H); 8.02 (d, J=9.2 Hz 1H); 8.73 (d, J=1.4 Hz, 1H). MS (EI) m/z 286.3 [M+H]⁺

35.c) [1-(2,3-Dihydrobenzo[1,4]dioxin-6-ylmethyl)-azepan-(4RS)-yl]-(6-methoxy-quinolin-4-ylmethyl)amine

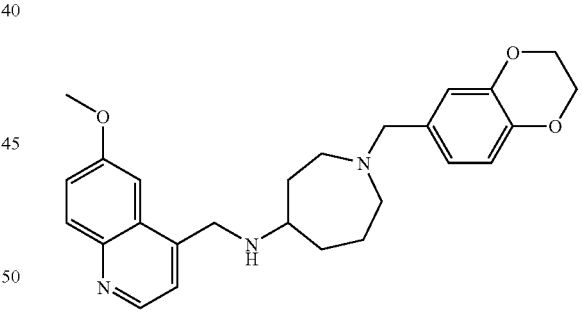

Sodium triacetoxyborohydride (100 mg, 0.47 mmol) was added to a solution of azepan-4-yl-(6-methoxy-quinolin-4-yl-methyl)amine (90 mg, 0.32 mmol) and 2,3-dihydrobenzo-[1,4]dioxin-6-carbaldehyde (51.8 mg, 0.32 mmol) in dichloroethane/THF (1:1, 0.7 ml). The reaction mixture was stirred at room temperature for 3 hours, concentrated and chromatographed on silica gel (ethyl acetate, methanol).

Yield: 56 mg (41%) ¹H-NMR (CDCl₃, 300 MHz): 1.40–2.05 (m, 6H); 2.35–2.80 (m, 3H); 2.8–2.9 (m, 1H); 3.41 (2, 2H); 3.99 (s, 3H); 4.15 (s, 2H); 4.20 (s, 4H); 6.70–6.80 (m, 3H); 7.37 (dd, J=2.76, J=9.1, 1H); 7.45 (d, J=2.76, 1H); 7.51 (d, J=4.4, 1H); 7.92 (d, J=9.12, 1H); 8.65 (d, J=4.4, 1H). MS (EI) m/z 434.7 [M+H]⁺

Example 36

(6-Methoxyquinolin-4-ylmethyl)-(1-phenethylazepan-(4RS)-yl)-amine

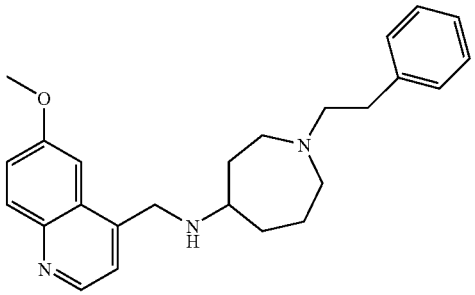

There was also prepared in a manner analogous to Example 35.c: (6-methoxy-quinolin-4-ylmethyl)-(1-phenethylazepan-(4RS)-yl)-amine (25% yield, MS (EI) m/z 390.5 [M+H]$^+$).

Example 37

(6-Methoxyquinolin-4-ylmethyl)-[1-(3-phenylpropyl)-azepan-4-yl]amine

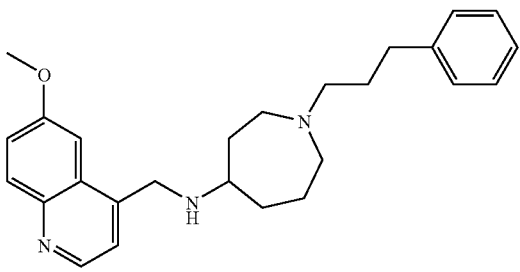

There was also prepared in a manner analogous to Example 35.c: (6-methoxy-quinolin-4-ylmethyl)-[1-(3-phenylpropyl)-azepan-4-yl]amine (25% yield, MS (EI) m/z 404.9 [M+H]$^+$)

Example 38

(1-Heptylazepan-(4RS)-yl)-(6-methoxyquinolin-4-ylmethyl)amine

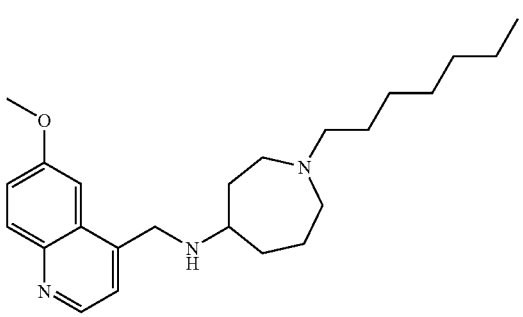

There was also prepared in a manner analogous to Example 35.c: (1-heptylazepan-(4RS)-yl)-(6-methoxy-quinolin-4-ylmethyl)amine (43% yield, MS (EI) m/z 384.4 [M+H]$^+$).

Example 39

1-{(4RS)-[(6-methoxy-quinolin-4-ylmethyl)amino]-azepan-1-yl}-3-phenylpropenone

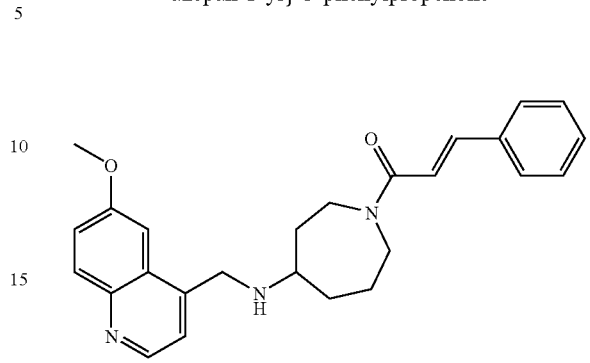

Cinnamic acid chloride (52.5 mg, 1 eq.) was added to a solution of azepan-4-yl-(6-methoxyquinolin-4-yl-methyl)amine (90 mg, 0.32 mmol) in THF/DCE. The reaction mixture was stirred at room temperature for 3 hours, concentrated, and purified by chromatography on silica gel (DCM/MeOH 9:1 (+1% NH$_4$OH)).

Yield: 37 mg (38%) MS (EI) m/z 416.6 [M+H]$^+$

Example 40

1-[(2RS)-Hydroxy-2-(6-methoxy-quinolin-4-yl)-ethyl]-4-phenethyl-[1,4]diazepane-(5RS)-carboxylic acid tert-butyl ester 40.a) 1-[2-Hydroxy-2-(6-methoxy-quinolin-4-yl)ethyl]-[1,4]-diazepane-5-carboxylic acid tert-butyl ester

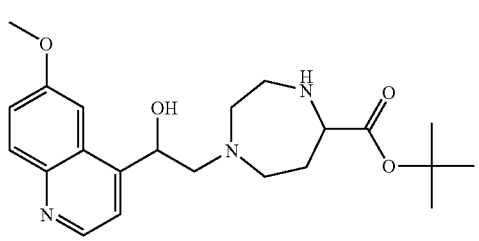

A mixture of 6-methoxy-4-oxiranylquinoline (400 mg, 2 mmol), [1,4]-diazepane-5-carboxylic acid tert-butyl ester (400 mg, 2 mmol, prepared as described in J. Chem. Research (S), 1991, 306, 2876), lithium perchlorate (211 mg, 2 mmol) and potassium carbonate (275 mg, 2 mmol) in DMF (5 ml) was heated at 100° C. for 4 hours. The reaction mixture was diluted with water and ethyl acetate, the aqueous phase was extracted with ethyl acetate and the combined organic phases were dried over sodium sulphate and concentrated. The product was purified by chromatography on silica gel (DCM/MeOH 9:1).

Yield: 330 mg (41%) MS (EI) m/z 402.5 [M+H]$^+$ 40.b) 1-[(2RS)-Hydroxy-2-(6-methoxy-quinolin-4-yl)ethyl]-4-phenethyl-[1,4]diazepane-(5RS)-carboxylic acid tert-butyl ester

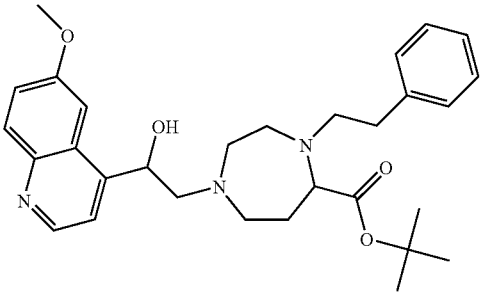

Sodium triacetoxyborohydride (79 mg (1.5 eq) was added to a solution of 1-[2-hydroxy-2-(6-methoxy-quinolin-4-yl)-ethyl]-[1,4]diazepane-5-carboxylic acid tert-butyl ester (100 mg, 0.25 mmol) and phenyl acetaldehyde (29.2 µl, 1 eq.) in THF (700 µl). After 2 hours, a further equivalent of phenyl acetaldehyde was added and the reaction mixture was heated to 40° C. After a further 2 hours, the reaction mixture was concentrated to dryness and purified by chromatography on silica gel (ethyl acetate, methanol).

Yield: 67 mg (54%) MS (EI) m/z 506 [M+H]$^+$ 40.c) 1-[(2RS)-Hydroxy-2-(6-methoxy-quinolin-4-yl)-ethyl]-4-phenethyl-[1,4]-diazepane-(5RS)-carboxylic acid

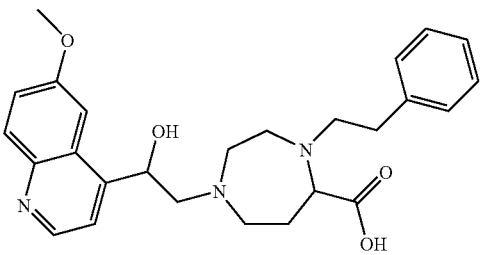

1-[2-Hydroxy-2-(6-methoxy-quinolin-4-yl)-ethyl]-4-phenethyl-[1,4]diazepane-5-carboxylic acid tert-butyl ester (55 mg) was suspended in 4M HCl in dioxane and stirred at room temperature for 3.5 hours. The reaction mixture was concentrated and purified by preparative HPLC.

Yield: 3.9 mg MS (EI) m/z 450 [M+H]$^+$

The following were also synthesised in analogous manner:

40.d) 1-[2-hydroxy-2-(6-methoxy-quinolin-4-yl)-ethyl]-4-(3-phenylpropyl)-[1,4]diazepane-5-carboxylic acid tert-butyl ester and 40.e) 1-[2-hydroxy-2-(6-methoxy-quinolin-4-yl)ethyl]-4-(3-phenylpropyl)-[1,4]diazepane-5-carboxylic acid starting from dihydrocinnamaldehyde.

In the same way, 40.f) 4-heptyl-1-[2-hydroxy-2-(6-methoxy-quinolin-4-yl)-ethyl]-[1,4]diazepane-5-carboxylic acid tert-butyl ester and 40.g) 4-heptyl-1-[2-hydroxy-2-(6-methoxy-quinolin-4-yl)-ethyl]-[1,4]diazepane-5-carboxylic acid were prepared starting from heptanal.

Example 41

2-[(RS)5-Hydroxymethyl-4-(3-phenylpropyl)-[1,4]diazepan-1-yl]-(1RS)-(6-methoxyquinolin-4-yl)-ethanol

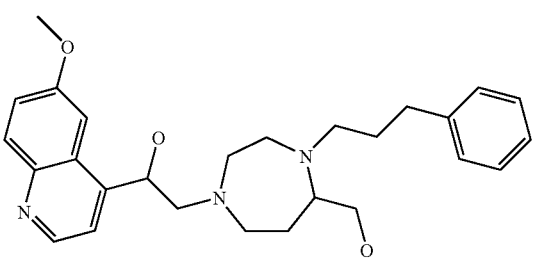

Lithium aluminium hydride (28 mg) was added to a solution of 1-[2-hydroxy-2-(6-methoxy-quinolin-4-yl)-ethyl]-4-(3-phenylpropyl)-[1,4]-diazepane-5-carboxylic acid tert-butyl ester (80 mg) in THF and stirring was carried out at room temperature for 1 hour. A few drops of saturated Rochelle salt solution were added to the reaction mixture, stirring was carried out for 15 minutes and the precipitate was filtered off.

Yield: 39 mg (57%) MS (EI) m/z 450 [M+H]$^+$

Starting from 4-heptyl-1-[2-hydroxy-2-(6-methoxy-quinolin-4-yl)-ethyl]-[1,4]diazepane-5-carboxylic acid tert-butyl ester, 2-(4-heptyl-5-hydroxy-methyl-[1,4]-diazepan-1-yl)-1-(6-methoxy-quinolin-4-yl)-ethanol was produced in an analogous manner in a yield of 33% (MS (EI) m/z 430 [M+H]$^+$).

Example 42

(2,3-Dihydro-benzo[1,4]dioxin-6-ylmethyl)-[4-(6-methoxy-quinazolin-4-yloxymethyl)-cyclohexyl]-amine 42.a) 4-(6-Methoxy-quinazolin-4-yloxymethyl)-cyclohexanol

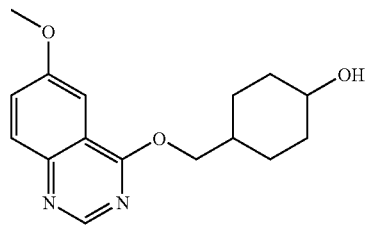

Sodium hydride (79 mg (1.5 eq.) was added at 0° C. to a solution of 4-hydroxymethyl-cyclohexanol (3 g, 12 mmol, synthesised analogously to J. Org. Chem. 1994 59 p. 2748–2761) in DMF (30 ml). After 20 minutes, a solution of 4-chloro-6-methoxy-quinazoline (1.94 g, 10 mmol) in DMF (10 ml) was added and the reaction mixture was heated to 40° C. After a further 2 hours, the reaction mixture was concentrated to dryness. The residue was diluted with water (100 ml) and ethyl acetate (100 ml), the phases were separated and the aqueous phase was extracted twice using 50 ml of ethyl acetate each time. The combined organic

42.b) 4-(6-Methoxy-quinazolin-4-yloxymethyl)-cyclohexanone

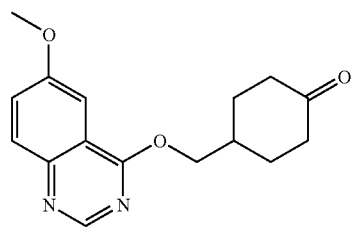

Triethylamine (10 ml, 71 mmol) and then, in portions, Pyr.SO3 (5.8 g, 36 mmol), were added at 0° C. to a solution of 4-(6-methoxy-quinazolin-4-yloxymethyl)-cyclohexanol (2.88 g, 10 mmol) in DMSO (30 ml). The reaction mixture was stirred at that temperature for 15 minutes and then allowed to come to room temperature. After 2 hours, water (300 ml) was added. The aqueous phase was extracted with ether (3×150 ml). The combined organic phases were washed with saturated sodium chloride solution, dried over MgSO$_4$ and concentrated. The crude product was purified by chromatography on silica gel (EtOAc/hex 1/2).

Yield: 2.6 g, 9.1 mmol MS (EI) m/z 287.1 [M+H]$^+$

42.c) Benzyl-[4-(6-methoxy-quinazolin-4-yloxymethyl)-cyclohexyl]-amine

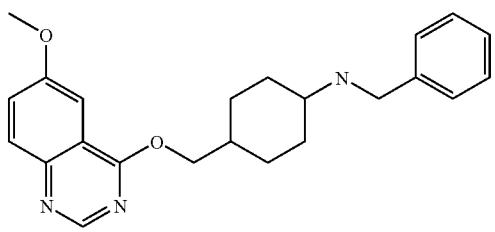

Benzylamine (1.08 ml, 10 mmol) and sodium cyanoborohydride (2.2 g, 11 mmol) were added to a solution of 4-(6-methoxy-quinazolin-4-yloxymethyl)-cyclohexanone (2.87 g, 10 mmol) in methanol (50 ml). The mixture was stirred overnight at room temperature. The reaction mixture was concentrated and the residue was dissolved in saturated potassium carbonate solution and ethyl acetate. The aqueous phase was extracted with ethyl acetate (2×50 ml), and the combined organic phases were dried over magnesium sulphate and concentrated. The residue was purified by column chromatography on silica gel (EtOAc and then EtOAc/MeOH 9/1).

Yield: 2.87 g, 10 mmol in the form of a cis/trans mixture MS (EI) m/z 287.1 [M+H]$^+$

42.d) 4-(6-Methoxy-quinazolin-4-yloxymethyl)-cyclohexylamine

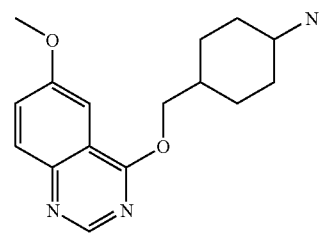

20% Pd(OH)$_2$ on carbon (1 g) was added to a solution of benzyl-[4-(6-methoxy-quinazolin-4-yloxymethyl)-cyclohexyl]-amine (2 g, 5.3 mmol) in MeOH (30 ml) and hydrogenation was carried out under a hydrogen atmosphere (1 bar) at 65° C. The reaction mixture was filtered and the filtrate was concentrated.

Yield: 1.44 g, 5 mmol in the form of a cis/trans mixture MS (EI) m/z 288 [M+H]$^+$

42.e) Title Compound

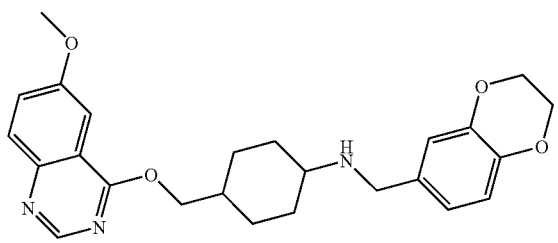

2,3-Dihydro-benzo[1,4]dioxin-6-carbaldehyde (0.045 g, 0.27 mmol) and then sodium triacetoxyborohydride (0.08 g, 0.377 mmol) were added to a solution of 4-(6-methoxyquinazolin-4-yloxymethyl)-cyclohexylamine (0.07 g, 0.25 mmol) in dichloroethane (1 ml). The reaction mixture was stirred for 2 hours and then filtered over Hydromatrix (wetted with NaHCO$_3$ solution, 2 ml) and subsequently washed with dichloromethane. The filtrate was concentrated to dryness by rotary evaporation. The residue was purified by column chromatography on silica gel (dichloromethane/MeOH 9/1 and then dichloromethane/MeOH 6/1).

Yield: 0.02 g (0.046 mmol) in the form of a cis/trans mixture MS (EI) m/z 436 [M+H]$^+$

Example 43

[4-(6-Methoxy-quinazolin-4-yloxymethyl)-cyclohexyl]-quinoxalin-2-ylmethyl-amine

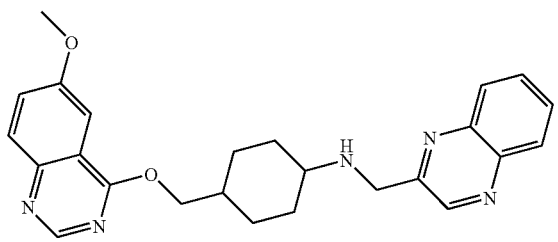

In analogy to Example 42.e, [4-(6-methoxy-quinazolin-4-yloxymethyl)-cyclohexyl]-quinoxalin-2-ylmethylamine was produced in a yield of 31% in the form of a cis/trans mixture (MS (EI) m/z 430 [M+H]+).

Example 44

6-{[4-(6-Methoxy-quinazolin-4-yloxymethyl)-cyclohexylamino]-methyl}-4H-benzo[1,4]oxazin-3-one

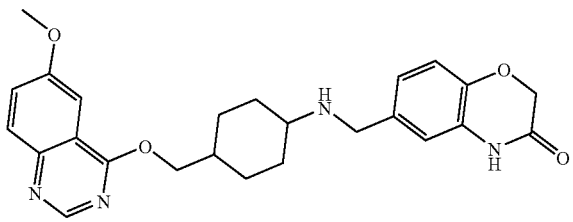

In analogy to Example 42.e, 6-{[4-(6-methoxy-quinazolin-4-yloxymethyl)-cyclohexylamino]-methyl}-4H-benzo[1,4]oxazin-3-one was produced in a yield of 38% in the form of a cis/trans mixture (MS (EI) m/z 448 [M+H]+).

Example 45

[4-(6-Methoxy-quinazolin-4-yloxymethyl)-cyclohexyl]-(3-phenyl-allyl)-amine

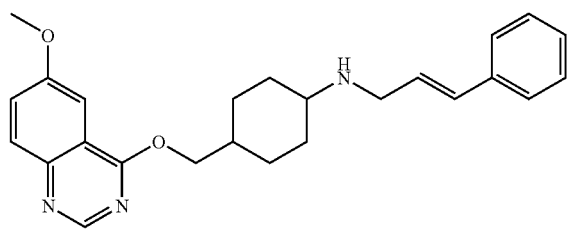

In analogy to Example 42.e, [4-(6-methoxy-quinazolin-4-yloxymethyl)-cyclohexyl]-(3-phenyl-allyl)-amine was produced in a yield of 25% in the form of a cis/trans mixture (MS (EI) m/z 405 [M+H]+).

Example 46

2-[4-(6-Methoxy-quinazolin-4-yloxymethyl)-cyclohexylamino]-N-pyridin-2-yl-acetamide

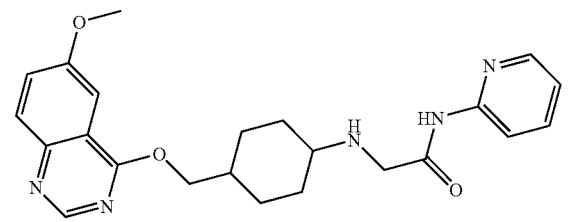

2-Bromo-N-pyridin-2-yl-acetamide (0.075 g, 0.35 mmol) and potassium carbonate (0.054 g, 0.39 mmol) were added to a solution of 4-(6-methoxy-quinazolin-4-yloxymethyl)-cyclohexylamine (0.1 g, 0.35 mmol) in DMF (3.5 ml). The reaction mixture was stirred at room temperature for 2 days and then concentrated to dryness by rotary evaporation. The residue was purified by column chromatography on silica gel (dichloromethane/MeOH 19/1 1% NH4OH).

Yield: 0.086 g (0.2 mmol) in the form of a cis/trans mixture MS (EI) m/z 422 [M+H]+

Example 47

(2,3-Dihydro-[1,4]dioxino[2,3-c]pyridin-7-ylmethyl)-[4-(6-methoxy-quinazolin-4-yloxymethyl)-cyclohexyl]-amine

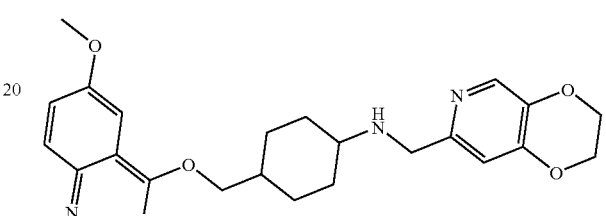

Starting from Example 42.e, was produced in an analogous manner in a yield of 55% in the form of a cis/trans mixture (MS (EI) m/z 437 [M+H]+).

Example 48

(2,3-Dihydro-benzo[1,4]dioxin-6-ylmethyl)-[4-(6-methoxy-quinolin-4-yloxymethyl)-cyclohexyl]-amine 48.a) trans-4-tert-Butoxycarbonylamino-cyclohexanecarboxylic acid

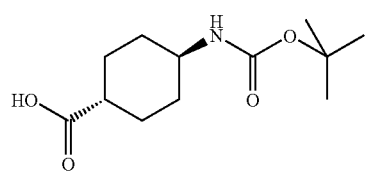

Di-tert-butyl dicarbonate (12 g, 55 mmol) dissolved in dioxane (50 ml) was added dropwise to a solution of trans-4-aminocyclohexanecarboxylic acid (Synth. Commun. 2002, 32, 1985) (7.16 g, 50 mmol) in dioxane (50 ml) and water (50 ml). After stirring for 30 minutes at room temperature, 1M NaOH (50 ml) was added and the reaction mixture was stirred overnight at room temperature. The dioxane was distilled off using a rotary evaporator and the aqueous residue was adjusted to pH 3 using 1N HCl and extracted with ethyl acetate. Organic extracts dried over Na2SO4 and concentrated.

Yield: 13.2 g MS (EI) m/z 242.4[M−H]−.

48.b) tert-Butyl trans-(4-hydroxymethyl-cyclohexyl)-carbamate

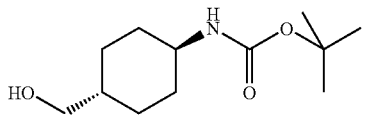

A solution of borane dimethyl sulphide complex (2.85 ml, 30 mmol) in THF (50 ml) was added dropwise at 0° C. to a solution of trans-4-tert-butoxycarbonylamino-cyclohexanecarboxylic acid (2.43 g, 10 mmol) in THF (100 ml). The reaction mixture was stirred at 0° C. for 15 minutes and at room temperature for 3 hours, methanol was cautiously added and the mixture was concentrated. The crude product was repeatedly treated with methanol and concentrated again, and finally dried under a high vacuum. Used without further purification.
Yield: 2.4 g (quant.)

48.c) trans-Methanesulphonic acid 4-tert-butoxycarbonyl-aminocyclohexylmethyl ester

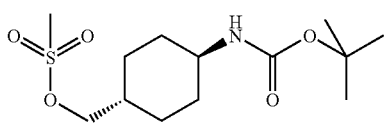

At 0° C., triethylamine (417 µl, 2.2 mmol) was added to a solution of tert-butyl trans-(4-hydroxymethylcyclohexyl)-carbamate (459 mg, 3 mmol) in dichloromethane (25 ml), and methanesulphonyl chloride (171 µl, 2.2 mmol) was added dropwise. The reaction mixture was stirred at 0° C. for 5 hours and at room temperature for 1 hour, taken up with water and extracted with dichloromethane. The organic phase was dried over $Na_2SO_4$ and concentrated. The crude product was reacted without further purification.

48.d) tert-Butyl [4-(6-methoxy-quinolin-4-yloxymethyl)-cyclohexyl]carbamate

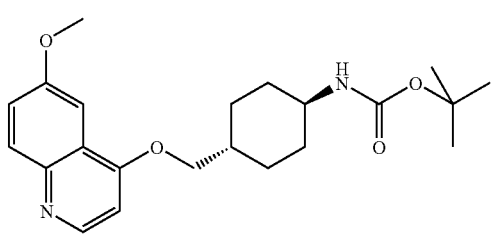

NaH dispersion (55% in mineral oil, 88 mg, 2 mmol) was added to a suspension of 6-methoxy-4-hydroxyquinoline (350 mg, 2 mmol) in DMF (4 ml) and stirred at room temperature until a solution formed. trans-Methanesulphonic acid 4-tert-butoxycarbonylaminocyclohexylmethyl ester (635 mg, 2 mmol) was added and the reaction mixture was stirred overnight at 80° C. Water was added to the mixture and extraction was carried out with ethyl acetate. Organic extracts washed with water, dried over $Na_2SO_4$ and concentrated. The crude product was purified by chromatography on silica gel (DCM/MeOH 9:1).
Yield: 438 mg, 56.6% (oil) (MS (EI) m/z 387 [M+H]⁺)

48.e) trans-4-(6-Methoxy-quinolin-4-yloxymethyl)-cyclohexylamine

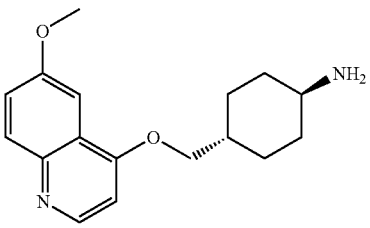

A solution of tert-butyl [4-(6-methoxy-quinolin-4-yloxymethyl)-cyclohexyl]carbamate (438 mg, 1.13 mmol) and TFA (1.5 ml) in dichloromethane (4 ml) was stirred at room temperature for 2 hours. The reaction mixture was poured onto ice/ammonium hydroxide and extracted with dichloromethane. The organic extracts were dried over $Na_2SO_4$ and concentrated.
Yield: 313 mg, 97% (MS (EI) m/z 287 [M+H]⁺).

48.f) Title Compound

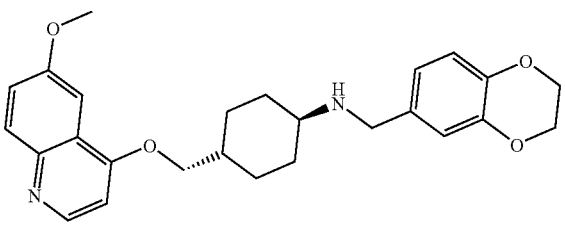

In analogy to Example 42.e, trans-2,3-dihydro-benzo[1,4]-dioxin-6-ylmethyl)-[4-(6-methoxy-quinolin-4-yloxymethyl)-cyclohexyl]-amine was produced in a yield of 73% (MS (EI) m/z 435 [M+H]⁺).

Example 49

6-{[4-(6-Methoxy-quinolin-4-yloxymethyl)-cyclohexylamino]-methyl}-4H-benzo[1,4]oxazin-3-one

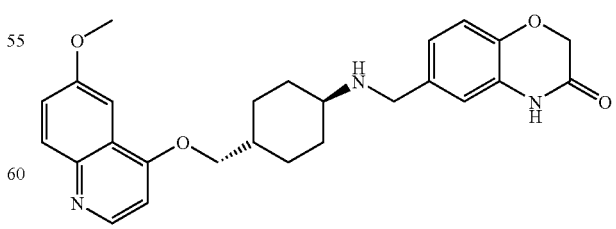

In analogy to Example 42.e, trans-6-{[4-(6-methoxy-quinolin-4-yloxymethyl)-cyclohexylamino]-methyl}-4H-benzo-[1,4]oxazin-3-one was produced in a yield of 81% (MS (EI) m/z 448 [M+H]⁺).

Example 50

(2,3-Dihydro-benzo[1,4]dioxin-6-ylmethyl)-[4-(6-methoxy-[1,5]naphthyridin-4-yloxymethyl)-cyclohexyl]-amine

50.a) 4-(6-Methoxy-[1,5]naphthyridin-4-yloxymethyl)-cyclohexylamine

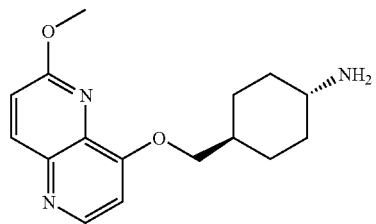

4-(6-Methoxy-[1,5]naphthyridin-4-yloxymethyl)cyclohexylamine was prepared analogously to Example 48 starting from 6-methoxy-[1,5]naphthyridin-4-ol.

50.b) Title Compound

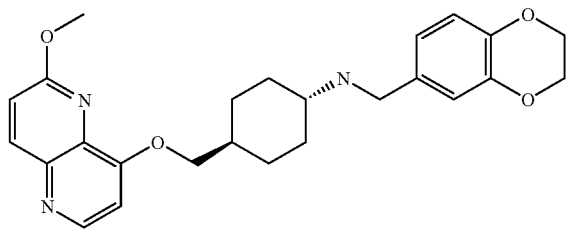

In analogy to Example 42.e, (2,3-dihydro-benzo[1,4]dioxin-6-ylmethyl)-[4-(6-methoxy-[1,5]naphthyridin-4-yloxymethyl)-cyclohexyl]-amine was produced in a yield of 55% (MS (EI) m/z 456.6 [M+H]$^+$).

Example 51

6-{[4-(6-Methoxy-[1,5]naphthyridin-4-yloxymethyl)-cyclohexylamino]-methyl}-4H-benzo[1,4]oxazin-3-one

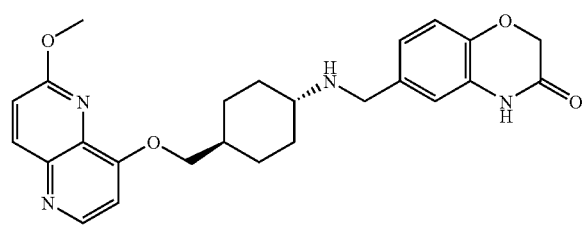

In analogy to Example 42.e, trans-6-{[4-(6-methoxy-[1,5]naphthyridin-4-yloxymethyl)-cyclohexylamino]-methyl}-4H-benzo[1,4]oxazin-3-one was produced in a yield of 79% (MS (EI) m/z 456.6 [M+H]$^+$).

Example 52

2-{3-[(2,3-Dihydro-benzo[1,4]dioxin-6-yl-methyl)-amino]-8-aza-bicyclo[3.2.1]oct-8-yl}-(1RS)-(6-methoxy-quinolin-4-yl)-ethanol

52.a) tert-Butyl {8-[(2RS)-hydroxy-2-(6-methoxy-quinolin-4-yl)-ethyl]-8-aza-bicyclo[3.2.1]oct-3-yl}carbamate

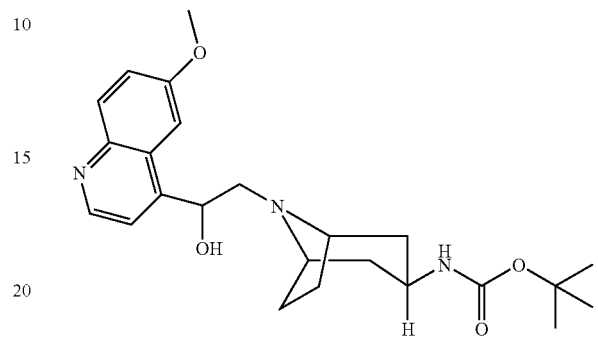

In analogy to Example 2.c, the title compound was produced in a yield of 82% (MS (EI) m/z 428 [M+H]$^+$).

tert-Butyl (8-aza-bicyclo[3.2.1]oct-3-yl)carbamate was prepared according to *Eur. J. Med. Chem.* 1991 (34) p. 646–653.

52.b) 2-{3-[(2,3-Dihydro-benzo[1,4]dioxin-6-ylmethyl)amino]-8-aza-bicyclo[3.2.1]oct-8-yl}-(1RS)-(6-methoxy-quinolin-4-yl)-ethanol

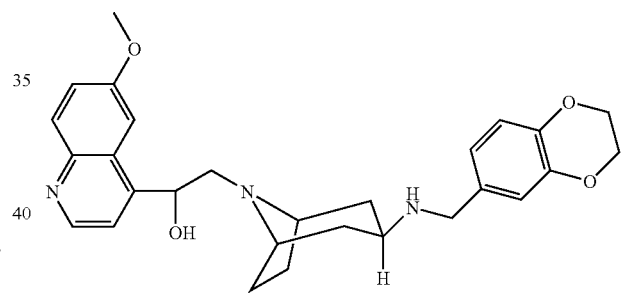

In analogy to Example 2.c, the title compound was produced in a yield of 86% (MS (EI) m/z 328 [M+H]$^+$).

Example 53

2-{3-[(Benzo[1,3]dioxol-5-ylmethyl)-amino]-8-aza-bicyclo[3.2.1]oct-8-yl}-(1RS)-(6-methoxy-quinolin-4-yl)-ethanol

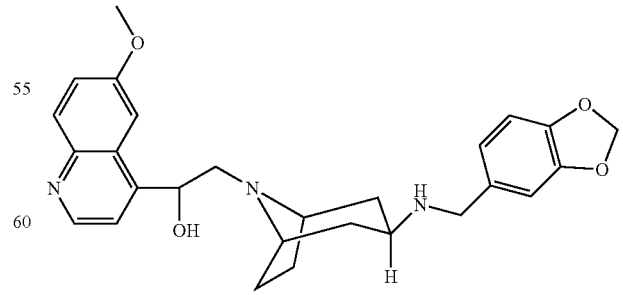

In analogy to Example 2.e, 2-{3-[(benzo[1,3]dioxol-5-ylmethyl)-amino]-8-aza-bicyclo[3.2.1]oct-8-yl}-1-(6-methoxy-quinolin-4-yl)-ethanol was produced in a yield of 62% (MS (EI) m/z 462 [M+H]$^+$).

Example 54

6-({8-[(2RS)-Hydroxy-2-(6-methoxy-quinolin-4-yl)-ethyl]-8-aza-bicyclo[3.2.1]oct-3-ylamino}-methyl)-4H-benzo[1,4]oxazin-3-one

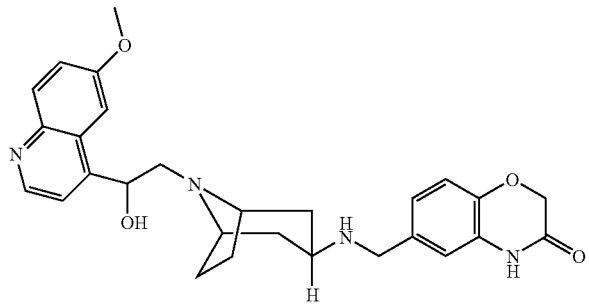

In analogy to Example 2.e, 6-({8-[2-hydroxy-2-(6-methoxy-quinolin-4-yl)-ethyl]-8-aza-bicyclo[3.2.1]oct-3-ylamino}-methyl)-4H-benzo[1,4]oxazin-3-one was produced in a yield of 7% (MS (EI) m/z 489 [M+H]$^+$).

Example 55

2-{3-[(Benzo[1,2,5]thiadiazol-5-ylmethyl)-amino]-8-aza-bicyclo[3.2.1]oct-8-yl}-(1RS)-(6-methoxy-quinolin-4-yl)-ethanol

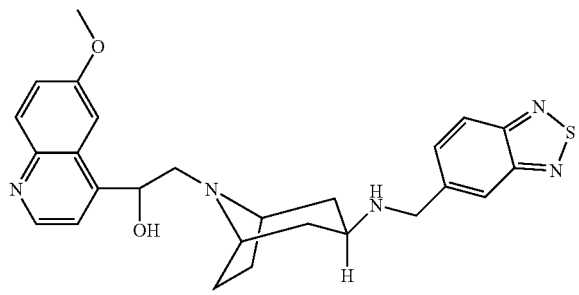

In analogy to Example 2.e, 2-{3-[(benzo[1,2,5]thiadiazol-5-ylmethyl)-amino]-8-aza-bicyclo[3.2.1]oct-8-yl}-1-(6-methoxy-quinolin-4-yl)-ethanol was produced in a yield of 59% (MS (EI) m/z 476 [M+H]$^+$)

Example 56

1-(6-Methoxy-quinolin-4-yl)-2-[3-(3-phenyl-allylamino)-8-aza-bicyclo[3.2.1]oct-8-yl]-ethanol

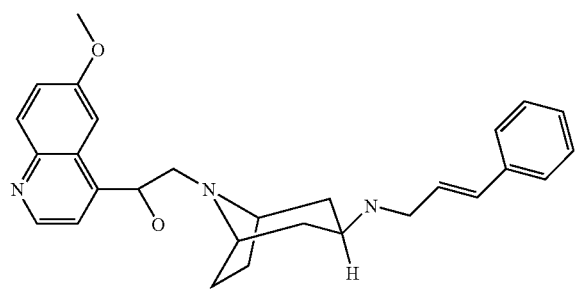

In analogy to Example 2.e, 1-(6-methoxy-quinolin-4-yl)-2-[3-(3-phenyl-allylamino)-8-aza-bicyclo[3.2.1]oct-8-yl]-ethanol was produced in a yield of 44% (MS (EI) m/z 445 [M+H]$^+$).

Example 57

2-[3-(3-Furan-2-yl-allylamino)-8-aza-bicyclo[3.2.1]oct-8-yl]-(1RS)-(6-methoxy-quinolin-4-yl)-ethanol

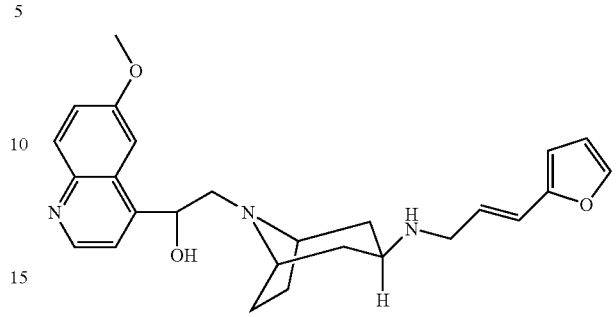

In analogy to Example 2.e, 2-[3-(3-furan-2-yl-allylamino)-8-aza-bicyclo[3.2.1]oct-8-yl]-1-(6-methoxy-quinolin-4-yl)-ethanol was produced in a yield of 51% (MS (EI) m/z 434 [M+H]$^+$).

Example 58

2-{3-[(Benzofuran-2-ylmethyl)-amino]-8-aza-bicyclo[3.2.1]oct-8-yl}-(1RS)-(6-methoxy-quinolin-4-yl)-ethanol

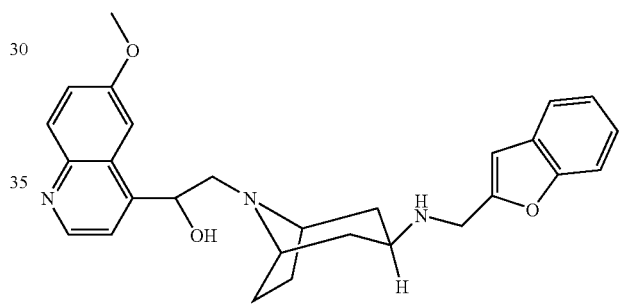

In analogy to Example 2.e, 2-{3-[(benzofuran-2-ylmethyl)-amino]-8-aza-bicyclo[3.2.1]oct-8-yl}-1-(6-methoxy-quinolin-4-yl)-ethanol was produced in a yield of 62% (MS (EI) m/z 458 [M+H]$^+$).

Example 59

2-(5-{[(2,3-Dihydro-benzo[1,4]dioxin-6-ylmethyl)-amino]-methyl}-3,6-dihydro-2H-pyridin-1-yl)-1-(6-methoxy-quinolin-4-yl)-ethanol 59.a) tert-Butyl 5-azidomethyl-3,6-dihydro-2H-pyridine-1-carbamate

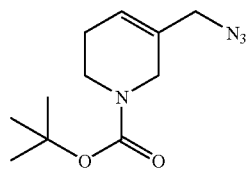

At 0° C., triethylamine (3.7 ml, 26.2 mmol) and, dropwise, methanesulphonyl chloride (1.2 ml, 15.44 mmol) were added to a solution of tert-butyl 5-hydroxymethyl-3,6-dihydro-2H-pyridine-1-carbamate (Tetrahedron 1998, 54, 7045–7056, 2.8 g, 13.1 mmol) in DCM (50 ml). The reaction mixture was stirred at 0° C. for 20 minutes before a saturated solution of NaHCO3 (40 ml) was added, and the two phases were separated. The aqueous phase was extracted with dichloromethane (40 ml). The combined organic phases were washed with saturated sodium chloride solution and dried over MgSO₄ and concentrated. The crude product was dissolved in DMF (50 ml), and sodium azide (1.7 g, 26.1 mmol) was added. The mixture was heated to 80° C. Reaction monitored by LCMS. Once the reaction was complete, the mixture was cooled and concentrated. The residue was taken up in EtOAc and water and the aqueous phase was extracted with EtOAc (2×100 ml). The combined organic phases were washed with saturated sodium chloride solution, dried over MgSO₄ and concentrated. The residue was purified by chromatography on silica gel (EtOAc/hex 1/6).

Yield: (2.2 g, 9.23 mmol) Oil. MS (EI) m/z 239.4 [M+H]⁺.

59.b) tert-Butyl 5-aminomethyl-3,6-dihydro-2H-pyridine-1-carbamate

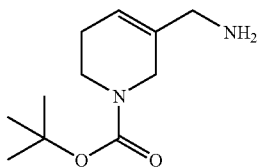

Triphenylphosphine on polystyrene (5.24 g) was added to a solution of tert-butyl 5-azidomethyl-3,6-dihydro-2H-pyridine-1-carbamate (1 g, 4.2 mmol) in THF (25 ml) and water (0.250 ml). The reaction mixture was shaken at room temperature for 36 hours. The polymer was filtered off and then washed with THF. The filtrate was concentrated.

Yield: (0.893 g, 4.2 mmol) MS (EI) m/z 213.4 [M+H]⁺.

59.c) tert-Butyl 5-{[(2,3-dihydro-benzo[1,4]dioxin-6-ylmethyl)-amino]-methyl}-3,6-dihydro-2H-pyridine-1-carbamate

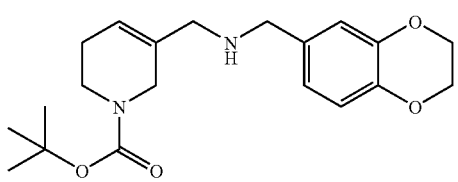

A solution of tert-butyl 5-aminomethyl-3,6-dihydro-2H-pyridine-1-carbamate (0.7 g, 3.3 mmol) and 1,4-benzodioxane-6-carbaldehyde (0.54 g, 3.3 mmol) in THF (2 ml) and DCE (4 ml) was stirred at room temperature for 1 hour. Sodium triacetoxyborohydride (0.770 g, 3.81 mmol) was then added thereto. The reaction mixture was stirred at room temperature for 5 hours and filtered through Hydromatrix (wetted with saturated NaHCO₃ solution) and the filtrate was concentrated. The residue was purified by chromatography on silica gel (EtOAc/hex 2/1 and then EtOAc/MeOH 9/1).

Yield: 0.16 g, 0.44 mmol (oil). MS (EI) m/z 361 [M+H]⁺.

59.d) (2,3-Dihydro-benzo[1,4]dioxin-6-ylmethyl)-(1,2,5,6-tetrahydropyridin-3-ylmethyl)-amine

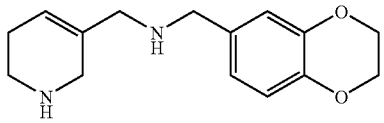

A solution of tert-butyl 5-{[(2,3-dihydro-benzo[1,4]-dioxin-6-ylmethyl)-amino]-methyl}-3,6-dihydro-2H-pyridine-1-carbamate (0.16 g, 0.44 mmol) in TFA (3 ml) was stirred at room temperature for 30 minutes, concentrated and taken up in saturated bicarbonate solution (30 ml) and dichloromethane (30 ml). The aqueous phase was extracted with dichloromethane (2×30 ml) and the combined organic phases were washed with saturated sodium chloride solution, dried over MgSO₄ and concentrated.

Yield: 0.06 g, 0.23 mmol, 52% (oil) MS (EI) m/z 261 [M+H]⁺.

59.e) Title Compound

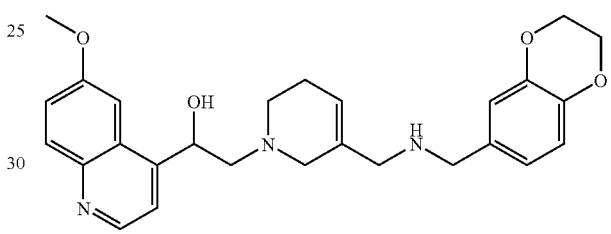

A solution of (2,3-dihydro-benzo[1,4]dioxin-6-ylmethyl)-(1,2,5,6-tetrahydro-pyridin-3-ylmethyl)-amine (0.06 g, 0.23 mmol) and 6-methoxy-4-oxiranylquinoline (0.06 g, 0.29 mmol) in EtOH (2 ml) was heated at 80° C. for 14 hours. The reaction mixture was concentrated and the residue was purified by chromatography on silica gel (DCM/MeOH 9/1).

Yield: 0.025 g, 0.054 mmol, 23% (foam) MS (EI) m/z 462 [M+H]⁺.

Example 60

2-((2RS)-{[(Benzo[1,3]dioxol-5-ylmethyl)-amino]-methyl}-morpholin-4-yl)-(1RS)-(6-methoxy-quinolin-4-yl)-ethanol

60.a) (2RS)-Azidomethyl-4-benzyl-morpholine

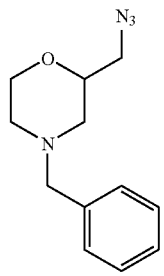

At 0° C., triethylamine (4.88 g, 48.25 mmol) and, dropwise, methansulphonyl chloride (2.25 ml, 28.95 mmol) were added to a solution of N-benzyl-2-hydroxymethylmorpholine (*Synthetic Communications*, 1980, 10 (1), 59–73, 5 g, 24.12 mmol) in DCM (60 ml). After 30 minutes, the reaction was terminated by addition of saturated bicarbonate solution (50 ml). The organic phase was washed with saturated sodium chloride solution (50 ml), dried over MgSO₄ and concentrated.

The crude product was dissolved in DMF (50 ml), and sodium azide (3.11 g, 47.8 mmol) was added. The mixture was heated overnight at 80° C. The mixture was cooled and concentrated. The residue was taken up in ether (100 ml) and water (50 ml) and the aqueous phase was extracted with ether (2×100 ml). The combined organic phases were washed with saturated sodium chloride solution, dried over MgSO₄ and concentrated. The residue was purified by chromatography on silica gel (EtOAc).

Yield: (4.23 g, 18 mmol, 75%) Oil. MS (EI) m/z 236.2 [M+H]⁺.

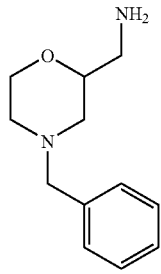

60.b) 2-(4-Benzyl-morpholin-(2RS)-yl)-methylamine

A solution of 2-Azidomethyl-4-benzyl-morpholine (4.23 g, 18 mmol) and triphenylphosphine (9.47 g, 36 mmol) in THF/water (10/1, 100 ml) was heated overnight at 60° C. The reaction mixture was concentrated and the residue was taken up in 3N HCl (200 ml) and EtOAc (200 ml). The aqueous phase was extracted with EtOAc (4*). The aqueous phase was adjusted to pH 12 using NaOH and extracted with EtOAc (2×200 ml), dried over MgSO₄ and concentrated.

Yield: (3.64 g, 16.8 mmol, 93%) Oil. MS (EI) m/z 207.2 [M+H]⁺.

60.c) tert-Butyl (4-benzyl-morpholin-(2RS)-ylmethyl)-carbamate

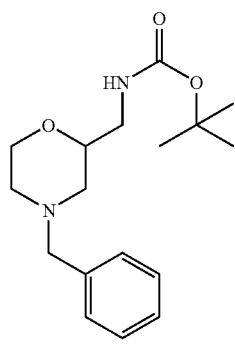

At 0° C., triethylamine (1.78 g, 17.74 mmol) and di-tert-butyl dicarbonate (2.32 g, 10.65 mmol) were added to a solution of 2-(4-benzyl-morpholin-2-yl)-methylamine (1.83 g, 8.87 mmol) in DCM (45 ml). The reaction mixture was stirred at that temperature for 30 minutes and concentrated. The residue was purified by chromatography on silica gel (EtOAc/hex 1:1).

Yield: (1.51 g, 4.93 mmol, 51%) Oil. MS (EI) m/z 307.3 [M+H]⁺.

60.d) tert-Butyl {4-[(2RS)-hydroxy-2-(6-methoxy-quinolin-4-yl)-ethyl]-morpholin-(2RS)-ylmethyl}carbamate

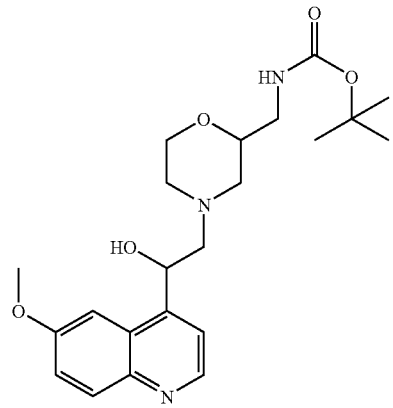

20% Pd(OH)₂ (0.7 g) was added to a solution of tert-butyl (4-benzyl-morpholin-2-ylmethyl)carbamate (1.51 g, 4.93 mmol) in THF:MeOH (1/1, 28 ml). The reaction mixture was stirred for 2 hours under a hydrogen atmosphere. The mixture was filtered and the filtrate was concentrated. The intermediate was dissolved in DMF (15 ml), and 6-methoxy-4-oxiranylquinoline (0.9 g, 4.48 mmol), lithium perchlorate (0.477 g, 4.48 mmol) and potassium carbonate (0.743 g, 5.376 mmol) were added. The mixture was heated at 80° C. for 23 hours. After cooling, filtration was carried out and the filtrate was concentrated. The residue was dissolved in EtOAc and washed with water, dried over MgSO₄ and concentrated. The residue was purified by chromatography on silica gel (DCM:MeOH 9:1).

Yield: (1 g, 2.4 mmol, 48%) Oil. MS (EI) m/z 418.5 [M+H]⁺.

60.e) 2-((2RS)-Aminomethyl-morpholin-4-yl)-(1RS)-(6-methoxy-quinolin-4-yl)-ethanol

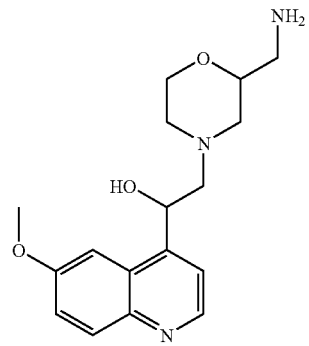

TFA (2.5 ml) was added at 0° C. to a solution of tert-butyl {4-[2-hydroxy-2-(6-methoxy-quinolin-4-yl)-ethyl]-morpholin-2-ylmethyl}carbamate (0.95 g, 2.27 mmol) in DCM (4 ml). The reaction mixture was stirred at room temperature for 1.5 hours and concentrated. The residue was taken up in DCM/MeOH (9/1, 30 ml) and ammonium hydroxide (20 ml). The aqueous phase was extracted with DCM/MeOH (2×30 ml) and the combined organic phases were dried over Na₂SO₄ and concentrated.

Yield: (0.718 g, 2.25 mmol, 99%) Oil. MS (EI) m/z 318.5 [M+H]⁺.

60.f) 2-(2-{[(Benzo[1,3]dioxol-5-ylmethyl)-amino]-methyl}-morpholin-4-yl)-1-(6-methoxy-quinolin-4-yl)-ethanol

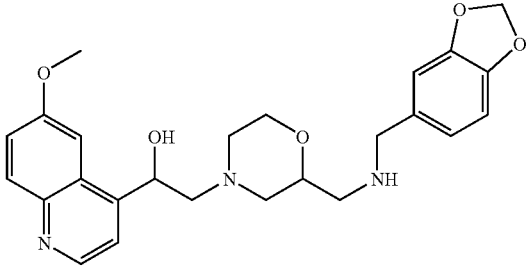

Activated 3A molecular sieve (3.485 g) and piperonal (0.172 g, 1.15 mmol) were added to a solution of 2-(2-aminomethyl-morpholin-4-yl)-1-(6-methoxy-quinolin-4-yl)-ethanol (0.365 g, 1.15 mmol) in DCM (10.5 ml) and methanol (3.5 ml). The mixture was stirred overnight at room temperature before sodium borohydride (0.112 g, 2.9 mmol) was added. The reaction mixture was stirred at room temperature for a further 2 hours, filtered over Hydromatrix (wetted with NaHCO$_3$) and concentrated. The residue was purified by chromatography on silica gel (DCM:MeOH 9:1+1% NH$_4$OH).

Yield: (0.261 g, 0.57 mmol, 50%) Oil. MS (EI) m/z 452.5 [M+H]$^+$.

Example 61

2-((2RS)-{[(2,3-Dihydro-benzo[1,4]dioxin-6-ylmethyl)-amino]-methyl}-morpholin-4-yl)-(1RS)-(6-methoxy-quinolin-4-yl)-ethanol

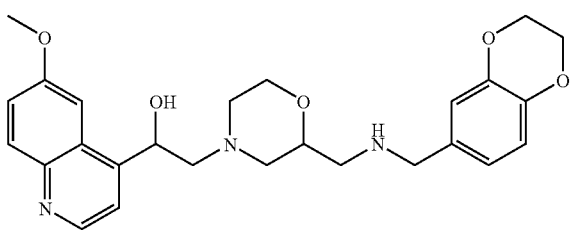

Analogously to Example 60.f, also 2-(2-{[(2,3-dihydro-benzo[1,4]dioxin-6-ylmethyl)-amino]-methyl}-morpholin-4-yl)-1-(6-methoxy-quinolin-4-yl)-ethanol was produced in a yield of 33% (MS (EI) m/z 466 [M+H]$^+$.)

Anti-Bacterial Activity:

The MHK (μg/ml) of those compounds was measured in relation to the following bacterial strains: *S. aureus* ATCC 29213, *S. aureus* 16, *E. faecalis* ATCC 29212, *E. faecium* vanA E25-1, *H. influenzae* 11, *E. coli* ATCC 25922, *M. catarrhalis* 117, *S. pneumoniae* ATCC 49619. Examples 5–6, 8, 11–16, 18–26, 30, 44–45, 47–58 have an MHK<=0.125 in relation to at least one of the listed strains.

Examples 1–4, 7, 9–10, 17, 27–29, 34, 42, 43, 46, 59, 61 have a MHK<=0.5 in relation to at least one of the listed strains.

The invention claimed is:

1. Compounds of formula (I):

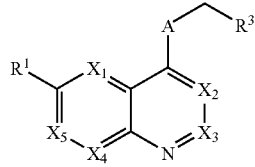

wherein A is an oxygen, sulphur or nitrogen atom or a C$_{1-4}$alkylene, C$_{2-4}$alkenylene, C$_{2-4}$alkynylene or C$_{1-4}$heteroalkylene group, $X_1$, $X_2$, $X_3$, $X_4$ and $X_5$ groups of formula CR$^2$, R$^1$ is a hydrogen atom, a halogen atom, a hydroxy group, an alkyloxy group or a heteroalkyloxy group, R$^2$ is a hydrogen atom, a halogen atom, or a hydroxy, alkyl, alkenyl, alkynyl or heteroalkyl group, R$^3$ is selected from the following groups:

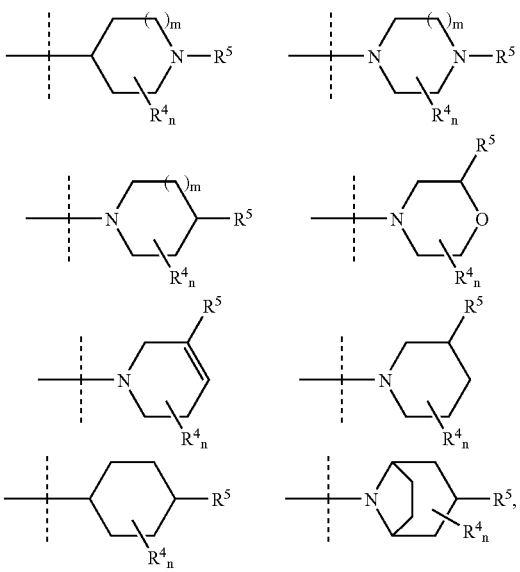

the radicals R$^4$, each independently of any other(s), are a hydroxy group, a C$_{1-6}$alkyl group or a C$_{1-8}$heteroalkyl group, R$^5$ is an alkyl, alkenyl, alkynyl, heteroalkyl, aryl, heteroaryl, cycloalkyl, alkylcycloalkyl, heteroalkyl-cycloalkyl, heterocycloalkyl, aralkyl or heteroaralkyl radical, n is 0, 1, 2 or 3 and m is 0 or 2, or a pharmacologically acceptable salt, solvate, hydrate or a pharmacologically acceptable formulation thereof.

2. Compounds according to claim 1, wherein A is an oxygen atom or a group of formula CH$_2$ or CH(OH).

3. Compounds according to claim 1, wherein all of the groups $X_1$, $X_2$, $X_3$, $X_4$ and $X_5$ are CH groups.

4. Compounds according to claim 1, wherein R$^1$ is a halogen atom, a C$_{1-6}$alkyloxy group, a methyl group or an ethyl group.

5. Compounds according to claim 1, wherein R$^1$ is a methoxy group.

6. Compounds according to claim 1, wherein $R^4$ is a $C_{1-6}$heteroalkyl group having one or two oxygen atoms as individual hetero atoms.

7. Compounds according to claim 1, wherein $R^4$ is a group of formula —COOH, —CH$_2$COOH, —CH$_2$CH$_2$COOH, —CH$_2$COOCH$_3$, —CH$_2$CH$_3$, —CH$_2$OH, —CH$_2$CH$_2$OH, —OH, —OCH$_3$, —CH$_2$OCONH$_2$, —CH$_2$CH$_2$COOCH$_3$, —COOCH$_3$, —CH$_3$ or —(CH$_2$)$_3$OH.

8. Compounds according to claim 1, wherein n is 0 or 1.

9. Compounds according to claim 1, wherein $R^5$ is an aralkyl group or a heteroaralkyl group.

10. Compounds according to claim 1, wherein $R^5$ is a group of formula —Y-Cy, Y being a $C_1$–$C_6$alkylene, $C_2$–$C_6$alkenylene or $C_1$–$C_6$heteroalkylene group, wherein optionally a hydrogen atom may have been replaced by a hydroxy group or two hydrogen atoms may have been replaced by an =O group, and Cy being an optionally substituted phenyl, naphthyl or heteroaryl group containing 1 or 2 rings and from 5 to 10 ring atoms, or an optionally substituted arylheterocycloalkyl or heteroarylheterocycloalkyl group containing two rings and 9 or 10 ring atoms.

11. Compounds according to claim 1, wherein $R^3$ is selected from the following groups:

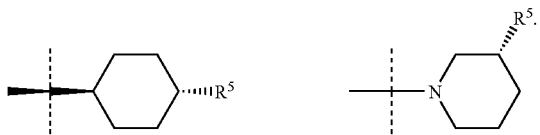

12. Pharmaceutical compositions that comprise a compound according to claim 1 and, optionally, carrier substances and/or adjuvants.

13. A method of using a compound or of a pharmaceutical composition according to claim 1 in the treatment of bacterial infections.

* * * * *